US010300112B2

(12) United States Patent
Ayares

(10) Patent No.: US 10,300,112 B2
(45) Date of Patent: May 28, 2019

(54) TRANSGENIC UNGULATES EXPRESSING CTLA4-IG AND USES THEREOF

(75) Inventor: David Lee Ayares, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 0 days.

(21) Appl. No.: 13/474,120

(22) Filed: May 17, 2012

(65) Prior Publication Data
US 2013/0202569 A1  Aug. 8, 2013

Related U.S. Application Data

(63) Continuation of application No. 11/990,246, filed as application No. PCT/US2006/030842 on Aug. 9, 2006, now abandoned.

(60) Provisional application No. 60/706,843, filed on Aug. 9, 2005.

(51) Int. Cl.
| | | |
|---|---|---|
| A01K 67/027 | (2006.01) | |
| A61K 38/17 | (2006.01) | |
| C07K 14/705 | (2006.01) | |
| C12N 15/85 | (2006.01) | |

(52) U.S. Cl.
CPC .... A61K 38/1774 (2013.01); C07K 14/70521 (2013.01); C12N 15/85 (2013.01); C12N 15/8509 (2013.01); *A01K 2217/05* (2013.01); *A01K 2227/108* (2013.01); *A01K 2267/02* (2013.01); *A01K 2267/025* (2013.01); *C07K 2319/30* (2013.01); *C12N 2830/008* (2013.01)

(58) Field of Classification Search
CPC ............... A61K 38/1774; C12N 15/85; C12N 15/8509; C12N 2830/008; C07K 14/70521; C07K 2319/30; A01K 2217/05; A01K 2267/025; A01K 2267/02; A01K 2227/108
USPC ........................................................ 800/17
See application file for complete search history.

(56) References Cited

U.S. PATENT DOCUMENTS

| | | | |
|---|---|---|---|
| 5,977,318 A | 11/1999 | Linsley et al. | |
| 6,423,316 B1 | 7/2002 | Riesbeck et al. | |
| 2002/0127205 A1* | 9/2002 | Edge ............................ | 424/93.2 |
| 2002/0192820 A1 | 12/2002 | Reff et al. | |
| 2003/0022836 A1* | 1/2003 | Larsen et al. .................... | 514/12 |
| 2003/0157705 A1* | 8/2003 | Fodor et al. ................... | 435/325 |
| 2004/0268424 A1 | 12/2004 | Phelps | |
| 2005/0260176 A1 | 11/2005 | Ayares et al. | |
| 2011/0038841 A1 | 2/2011 | Ayares et al. | |

FOREIGN PATENT DOCUMENTS

| | | |
|---|---|---|
| WO | WO 97/12035 | 4/1997 |
| WO | WO 98/42850 | 10/1998 |
| WO | WO 1998/042850 | 10/1998 |
| WO | WO 1999/057266 | 11/1999 |
| WO | WO 2001/030966 | 5/2001 |
| WO | WO 2004/016742 | 2/2004 |
| WO | WO 2004/028243 | 4/2004 |
| WO | WO 11/020120 | 2/2011 |

OTHER PUBLICATIONS

Mirenda, Apr. 2005, Diabetes, 54:1048-1055.*
Phelps (2009, Xenotransplantation, 16:477-485).*
Martin, Aug. 2005, Transgenic Research, 14:373-384.*
Sutherland, Transplantation, 2000,69:1806-1812.*
Phelps (2003, Science, 299:411-414).*
Lui (2003, Jour Immunol Methods, 277:171-183.*
Bottino, 2014, American Journal of Transplantation, 14:2275-2287.*
Ekser, 2012, The Lancet, 379:672-683.*
Satyananda, Transplantation, 2013, 96:937-945.*
Koshika, 2011, Immunology, 134:386-397.*
Phelps, CJ et al., "Production and Characterization of Transgenic Pigs Expressing Porcine CTLa4-1g" Xenotransplantation Nov. 2009;16(6):477-85.
Tai et al., Progress in xenotransplantation following the introduction of gene-knockout technology. Transplant International, 2007, vol. 20, pp. 107-117.
D'Apice et al., Gene-modified pigs. Xenotransplantation, 2008, vol. 15, pp. 87-90.
Yamaoka et al., Regeneration therapy of pancreatic b cells: towards a cure for diabetes? Biochemical and Biophysical Research Communications, 2002, vol. 296, pp. 1039-1043.
Strahan et al., "Pig alpha 1,3 galactosyltransferase: a major target for genetic manipulation in xenotransplantation," Frontiers in Bioscience 1, Jul. 1996, 1 e, pp. 34-41.
Galili et al., "Man, apes, and Old World monkeys differ from other mammals in the expression of alpha-galactosyl epitopes on nucleated cells," Journal of 8iological Chemistry, Nov. 1988, 263(33), pp. 17755-17762.
Cooper et al., "Genetically engineered pigs," Lancet, Sep. 1993, 342(8872), pp. 682-683.
Phelps et al., "Production of a 1,3-galactosyltransferase-deficient pigs," Science, Jan. 2003, 299, pp. 411-414.
Dumont, Francis J., "CTLA4-1g fusion proteins: promise for improved therapy of transplant rejection and autoimmune diseases," Therapy, Nov. 2004, 1(2), pp. 289-304.
Dariavach et al., "Human 1g superfamily CTLA-4 gene: chromosomal localization and identity of protein sequence between murine and human CTLA-4 cytoplasmic domains," European Journal of Immunology, Dec. 1988, 18(12), pp. 1901-1905.

(Continued)

*Primary Examiner* — Valarie E Bertoglio
(74) *Attorney, Agent, or Firm* — King & Spalding

(57) ABSTRACT

The present invention provides ungulates, including pigs, expressing CTLA4-Ig, as well as tissue, organs, cells and cell lines derived from such animals. Such animals, tissues, organs and cells can be used in research and medical therapy, including xenotransplanation. In addition, methods are provided to prepare organs, tissues and cells expressing the CTLA4-Ig for use in xenotransplantation, and nucleic acid constructs and vectors useful therein.

11 Claims, 12 Drawing Sheets

Specification includes a Sequence Listing.

(56) References Cited

OTHER PUBLICATIONS

Lafage-Pochitaloff et al., "Human CD28 and CTLA-41g superfamily genes are located on chromosome 2 at bands q33-q34," Immunogenetics, Mar. 1990, 31(3), pp. 198-201.

Vaughan et al., "Porcine CTLA4-Ig Lacks a MYPPPY Motif, 8inds InefficienUy to Human 87 and Specifically Suppresses Human CD4•T Cell Responses Costimulated by Pig but not Human 87\" Journal of Immunology, Sep. 2000, 165, pp. 3175-3181.

Ronchese et al., "Mice transgenic for a soluble form of murine CTLA-4 show enhanced expansion of antigen-specific CD4+ T cells and defective antibody production in vivom," J Exp Med, Mar. 1994, 179(3), pp. 809-817.

Lane et al., "8 cell function in mice transgenic for mCTLA4-H gamma 1: lack of germinal centers correlated with poor affinity maturation and class switching despite normal priming of CD4+ T cells," J Exp Med, Mar. 1994, 179(3), pp. 819-830.

Sutherland et al., "Protective effect of CTLA41g secreted by transgenic fetal pancreas allografts," Transplantation, May 2000, 69(9), pp. 1806-1812.

Liu et al., "Mammary gland-specific secretion of biologically acUve immunosuppressive agent cytotoxic-T-lymphocyte antigen 4 human immunoglobulin fusion protein (CTLA41g) in milk by transgenesis," J Immunol Methods, Jun. 2003, 277(1-2), pp. 171-183.

Martin et al., "Transgenic expression of CTLA4-Ig by fetal pig neurons for xenotransplantation," Transgenic Research, Aug. 2005, 14(4), pp. 373-384.

Cowan, Xenotransplantation, 2003, 10:223-231.

Feng, Sandy et al. Prolonged Xenograft Survival of Islets Infected with Small Doses of Adenovirus Expressing CTLA4Ig. Transplantation. vol. 67, 1607-1613, No. 12, Jun. 27, 1999.

Li, Tao-Sheng et al. Long-Term Survival of Xenografted Neonatal Cardiomyocytes by Adenvirus-Mediated CTLA4-Ig Expression and CD40 Blockade. American Heart Association Circulation. 2003. 108: 1760-1765, originally published Sep. 22, 2003.

Sabel, Michael S. et al. CTLA-4 Blockade Augments Human T Lymphocyte-Mediated Suppression of Lung Tumor Xenografts in SCID Mice. Cancer Immunol Immunother (2005) 54: 944-952. Published online Apr. 22, 2005.

Wang, Yong et al. Stable Skin-Specific Overexpression of Human CTLA4-Ig in Transgenic Mice Through Seven Generations. Acta Biochimica et Biophysica Sinica 2006, 38 (3): 171-178.

Zhai C et al., "Porcine CTLA4-Ig prolong islet xenografts in rats by downregulating the direct pathway of T-cell activation," Xenotransplantation 2011: 18: 40-45.

Wang et al, "Transgenic Expression of Cytotoxic T-Lymphocyte-Associated Antigen 4-Immunoglobulin Prolongs Xenogeneic Skin Graft Survival Without Extensive Immunosuppression in Rat Burn Wounds," J Trauma. 2008; 65:154-162.

Wang et al, "Transgenic expression of human cytoxic T-lymphocyte associated antigen4-Immunoglobulin (hCTLA4Ig) by porcine skin for xenogeneic skin grafting," Transgenic Res (2015) 24:199-211.

Shiraishi et al, "Adenovirus-Mediated Gene Transfer Using Ex Vivo Perfusion of the Heart Graft," Surg Today, Jpn J Surg (1996) 26:624-628.

Shiraishi et al, "Adenoviral Mediated Gene Transfer to the Porcine Liver In Vivo," Transplantation Proceedings, 30, 2914-2916 (1998).

Obushi et al, "Highly Effective Adenoviral Mediated Gene Transfer to Porcine Endothelial Cells In Vitro," Transplantation Proceedings, 30, 2917-2918 (1998).

* cited by examiner

FIGURE 1

```
        -30        -20        -10          1         11         21
MACSGFRSHG AWLELTSRTW PCTALFSLLF IPVFSKGMHV AQPAVVLANS RGVASFVCEY 31         41         51         61         71         81
GSAGKAAEVR VTVLRRAGSQ MTEVCAATYT VEDELTFLDD STCTGTSTEN KVNLTIQGLR 91        101        111        121        131        141
AVDTGLYICK VELLYPPPYY VGMGNGTQIY VIDPEPCPDS DFLLWILAAV SSGLFFYSFL 151        161        171        181
ITAVSLSKML KKRSPLTTGV YVKMPPTEPE CEKQFQPYFI PIN    SEQ ID:1 (pCTLA4)
```

FIGURE 2

```
1          11         21         31         41         51
ATGGCTTGCT CTGGATTCCG GAGCCATGGG GCTTGGCTGG AGCTTACTTC TAGGACCTGG 61         71         81         91         101        111
CCCTGTACAG CTCTGTTTTC TCTTCTCTTC ATCCCTGTCT TCTCCAAAGG GATGCACGTG 121        131        141        151        161        171
GCCCAACCTG CAGTAGTGCT GGCCAACAGC CGGGGTGTTG CCAGCTTTGT GTGTGAGTAT 181        191        201        211        221        231
GGGTCTGCAG GCAAAGCTGC CGAGGTCCGG GTGACAGTGC TGCGGCGGGC CGGCAGCCAG 241        251        261        271        281        291
ATGACTGAAG TCTGTGCCGC GACATATACT GTGGAGGATG AGTTGACCTT CCTTGATGAC 301        311        321        331        341        351
TCTACATGCA CTGGCACCTC CACCGAAAAC AAAGTGAACC TCACCATCCA AGGGCTGAGA 361        371        381        391        401        411
GCCGTGGACA CTGGGCTCTA CATCTGCAAG GTGGAGCTCC TGTACCCACC ACCCTACTAT 421        431        441        451        461        471
GTGGGTATGG GCAACGGGAC CCAGATTTAT GTCATTGATC CAGAACCATG CCCAGATTCT 481        491        501        511        521        531
GATTTCCTGC TCTGGATCCT GGCAGCAGTT AGTTCAGGGT TGTTTTTTTA CAGCTTCCTC 541        551        561        571        581        591
ATCACAGCTG TTTCTTTGAG CAAAATGCTA AAGAAAAGAA GTCCTCTTAC TACAGGGTC 601        611        621        631        641        651
TATGTGAAAA TGCCCCCGAC AGAGCCAGAA TGTGAAAAGC AATTTCAGCC TTATTTTATT 661        671
CCCATCAATT GA          SEQ ID: 2 (pCTLA4)
```

FIGURE 3

```
        -30        -20        -10          1         11         21
   MACSGFRSHG AWLELTSRTW PCTALFSLLF IPVFSKGMHV AQPAVVLANS RGVASFVCEY 31         41         51         61         71         81
   GSAGKAAEVR VTVLRRAGSQ MTEVCAATYT VEDELTFLDD STCTGTSTEN KVNLTIQGLR 91        101        111        121        131        141
   AVDTGLYICK VELLYPPPYY VGMGNGTQIY VIDPEPCPDS DGGSGGAAEP KSCDKTHTCP 151        161        171        181        191        201
   PCPAPELLGG PSVFLFPPKP KDTLMISRTP EVTCVVVDVS HEDPEVKFNW YVDGVEVHNA 211        221        231        241        251        261
   KTKPREEQYN STYRVVSVLT VLHQDWLNGK EYKCKVSNKA LPAPIEKTIS KAKGQPREPQ 271        281        291        301        311        321
   VYTLPPSRDE LTKNQVSLTC LVKGFYPSDI AVEWESNGQP ENNYKTTPPV LDSDGSFFLY 331        341        351        361
   SKLTVDKSRW QQGNVFSCSV MHEALHNHYT QKSLSLSPGK    SEQ ID NO. 3
``` pREV 785

FIGURE 5

```
TTAATTAAAATTATCTCTAAGGCATGTGAACTGGCTGTCTTGGTTTTCAT
CTGTACTTCATCTGCTACCTCTGTGACCTGAAACATATTTATAATTCCAT
TAAGCTGTGCATATGATAGATTTATCATATGTATTTTCCTTAAAGGATTT
TTGTAAGAACTAATTGAATTGATACCTGTAAAGTCTTTATCACACTACCC
AATAAATAATAAATCTCTTTGTTCAGCTCTCTGTTTCTATAAATATGTAC
AAGTTTTATTGTTTTTAGTGGTAGTGATTTTATTCTCTTTCTATATATAT
ACACACACATGTGTGCATTCATAAATATATACAATTTTTATGAATAAAAA
ATTATTAGCAATCAATATTGAAAACCACTGATTTTTGTTTATGTGAGCAA
ACAGCAGATTAAAAGGAATTCCTGCAGGAGTCAATGGGAAAAACCCATTG
GAGCCAAGTACACTGACTCAATAGGGACTTTCCATTGGGTTTTGCCCAGT
ACATAAGGTCAATAGGGGGTGAGTCAACAGGAAAGTCCCATTGGAGCCA
AGTACATTGAGTCAATAGGGACTTTCCAATGGGTTTTGCCCAGTACATAA
GGTCAATGGGAGGTAAGCCAATGGGTTTTTCCCATTACTGACATGTATAC
GCGTCGACGTCGGCGCGTTCAGCCTAAAGCTTTTTTCCCCGTATCCCCCCA
GGTGTCTGCAGGCTCAAAGAGCAGCGAGAAGCGTTCAGAGGAAAGCGAT
CCCGTGCCACCTTCCCCGTGCCCGGGCTGTCCCCGCACGCTGCCGGCTCGG
GGATGCGGGGGAGCGCCGGACCGGACCGGAGCCCCGGGCGGCTCGCTGC
TGCCCTAGCGGGGGAGGGACGTAATTACATCCCTGGGGGCTTTGGGGGGG
GGCTGTCCCTGCGGCCGCGAATTCGTAATCATGGTCATAGCTGTTTCCTGT
GTGAAATTGTTATCCGCTCACAATTCCACACAACATACGAGCCGGAAGCA
TAAAGTGTAAAGCCTGGGGTGCCTAATGAGTGAGCTAACTCACATTAATT
GCGTTGCGCTCACTGCCCGCTTTCCAGTCGGGAAACCTGTCGTGCCAGGG
GTCTAGCCGCGGTCTAGGAAGCTTTCTAGGGTACCTCTAGGGATCCACTA
GTTATTAATAGTAATCAATTACGGGGTCATTAGTTCATAGCCCATATATG
GAGTTCCGCGTTACATAACTTACGGTAAATGGCCCGCCTGGCTGACCGCC
CAACGACCCCCGCCCATTGACGTCAATAATGACGTATGTTCCCATAGTAA
CGCCAATAGGGACTTTCCATTGACGTCAATGGGTGGAGTATTTACGGTAA
ACTGCCCACTTGGCAGTACATCAAGTGTATCATATGCCAAGTACGCCCCC
TATTGACGTCAATGACGGTAAATGGCCCGCCTGGCATTATGCCCAGTACA
TGACCTTATGGGACTTTCCTACTTGGCAGTACATCTACGTATTAGTCATC
GCTATTACCATGGGTCGAGGTGAGCCCCACGTTCTGCTTCACTCTCCCCA
TCTCCCCCCCCTCCCCACCCCCAATTTTGTATTTATTTATTTTTTAATTA
TTTTGTGCAGCGATGGGGCGGGGGGGGGGGGCGCGCGCCAGGCGGG
GCGGGGCGGGGCGAGGGCGGGGCGGGGCGAGGCGGAGAGGTGCGGCG
GCAGCCAATCAGAGCGGCGCGCTCCGAAAGTTTCCTTTTATGGCGAGGCG
GCGGCGGCGGCGGCCCTATAAAAAGCGAAGCGCGCGGCGGGCGGGAGTC
GCTGCGTTGCCTTCGCCCCGTGCCCCGCTCCGCGCCGCCTCGCGCCGCCCG
CCCCGGCTCTGACTGACCGCGTTACTCCCACAGGTGAGCGGGCGGGACGG
CCCTTCTCCTCCGGGCTGTAATTAGCGCTTGGTTTAATGACGGCTCGTTTCT
TTTCTGTGGCTGCGTGAAAGCCTTAAAGGGCTCCGGGAGGGCCCTTTGTGC
GGGGGGGAGCGGCTCGGGGGGTGCGTGCGTGTGTGTGCGTGGGGAGC
G
```

FIGURE 5 (cont.)

CCGCGTGCGGCCCGCGCTGCCCGGCGGCTGTGAGCGCTGCGGGCGCGGCG
CGGGGCTTTGTGCGCTCCGCGTGTGCGCGAGGGGAGCGCGGCCGGGGGCG
GTGCCCCGCGGTGCGGGGGGGCTGCGAGGGGAACAAAGGCTGCGTGCGG
GGTGTGTGCGTGGGGGGGTGAGCAGGGGGTGTGGGCGCGGCGGTCGGGC
TGTAACCCCCCCTGCACCCCCTCCCCGAGTTGCTGAGCACGGCCCGGCT
TCGGGTGCGGGGCTCCGTGCGGGGCGTGGCGCGGGCTCGCCGTGCCGGG
CGGGGGGTGGCGGCAGGTGGGGGTGCCGGGCGGGGCGGGGCCGCCTCGG
GCCGGGGAGGGCTCGGGGGAGGGGCGCGGCGGCCCCGGAGCGCCGGCGG
CTGTCGAGGCGCGGCGAGCCGCAGCCATTGCCTTTTATGGTAATCGTGCG
AGAGGGCGCAGGGACTTCCTTTGTCCCAAATCTGGCGGAGCCGAAATCTG
GGAGGCGCCGCCGCACCCCCTCTAGCGGGCGCGGGCGAAGCGGTGCGGC
GCCGGCAGGAAGGAAATGGGCGGGGAGGGCCTTCGTGCGTCGCCGCGCC
GCCGTCCCCTTCTCCATCTCCAGCCTCGGGGCTGCCGCAGGGGGACGGCT
GCCTTCGGGGGGGACGGGGCAGGGCGGGGTTCGGCTTCTGGCGTGTGACC
GGCGGCTCTAGAGCCTCTGCTAACCATGTTCATGCCTTCTTCTTTTCCTAC
AGCTCCTGGGCAACGTGCTGGTTGTTGTGCTGTCTCATCATTTTGGCAAAG
AATTCCGCTGCGACTCGGCGGAGTCCCGGCGGCGCGTCCTTGTTCTAACCC
ggcgcgtGGTACCTCTAGAgtcgacGGTATCGATAAGCTTAGCCATGGCTT
GCTCTGGATTCCGGAGCCATGGGGCTTGGCTGGAGCTTACTTCTAGGACC
TGGCCCTGTACAGCTCTGTTTTCTCTTCTCTTCATCCCTGTCTTCTCCAA
AGGGATGCACGTGGCCCAACCTGCAGTAGTGCTGGCCAACAGCCGGGGTG
TTGCCAGCTTTGTGTGTGAGTATGGGTCTGCAGGCAAAGCTGCCGAGGTC
CGGGTGACAGTGCTGCGGCGGGCCGGCAGCCAGATGACTGAAGTCTGTGC
CGCGACATATACTGTGGAGGATGAGTTGACCTTCCTTGATGACTCTACAT
GCACTGGCACCTCCACCGAAAACAAAGTGAACCTCACCATCCAAGGGCTG
AGAGCCGTGGACACTGGGCTCTACATCTGCAAGGTGGAGCTCCTGTACCC
ACCACCCTACTATGTGGGTATGGGCAACGGGACCCAGATTTATGTCATTG
ATCCAGAACCATGCCCAGATTCTGATGGTGGCTCCGGTGGTGCTGCAGAG
CCCAAATCTTGTGACAAAACTCACACATGCCCACCGTGCCCAGGTAAGCC
AGCCCAGGCCTCGCCCTCCAGCTCAAGGCGGGACAGGTGCCCTAGAGTAG
CCTGCATCCAGGGACAGGCCCCAGCCGGGTGCTGACACGTCCACCTCCAT
CTCTTCCTCAGCACCTGAACTCCTGGGGGGACCGTCAGTCTTCCTCTTCC
CCCCAAAACCCAAGGACACCCTCATGATCTCCCGGACCCCTGAGGTCACA
TGCGTGGTGGTGGACGTGAGCCACGAAGACCCTGAGGTCAAGTTCAACTG
GTACGTGGACGGCGTGGAGGTGCATAATGCCAAGACAAAGCCGCGGGAG
GAGCAGTACAACAGCACGTACCGTGTGGTCAGCGTCCTCACCGTCCTGCA
CCAGGACTGGCTGAATGGCAAGGAGTACAAGTGCAAGGTCTCCAACAAA
GCCCTCCCAGCCCCCATCGAGAAAACCATCTCCAAAGCCAAAGGTGGGAC
CCGTGGGGTGCGAGGGCCACATGGACAGAGCCGGCTCGGCCCACCCTCTG
CCCTGGGAGTGACCGCTGTACCAACCTCTGTCCCTACAGGGCAGCCCCGA
GAACCACAGGTGTACACCCTGCCCCATCCCGGGATGAGCTGACCAAGAA
CCAGGTCAGCCTGACCTGCCTGGTCAAAGGCTTCTATCCCAGCGACATCG
CCGTGGAGTGGGAGAGCAATGGGCAGCCGGAGAACAACTACAAGGCCAC
GCCTCCCGTGCTGGACTCCGACGGCTCCTTCTTCCTCTACAGCAAGCTCAC
CGTGGACAAGAGCAGGTGGCAGCAGGGGAACGTCTTCTCATGCTCCGTGA
TGCATGAGGCTCTGCACAACCACTACACGCAGAAGAGCCTCTCCCTGTCT
CC

FIGURE 5 (cont.)

GGGTAAATGAGTGCGACGGCCGGCAAGCCCCGCTCCCCGGGCTCTCGCG
GTCGCACGAGGATGCTTGGCACGTACCCCGTGTACATACTTCCCGGGCGC
CCAGCATGGAAATAAAGCACCCAGCGCTGCCCTGGGCCCTGCGAGACTG
TGATGGTTCTTTCCACGGGTCAGGCCGAGTCTGAGGCCTGAGTGGCATGA
GGGAGGCAgcggccgcCATATGCATcctagcTGGCCAGACATGATAAGAT
ACATTGATGAGTTTGGACAAACCACAACTAGAATGCAGTGAAAAAAATGC
TTTATTTGTGAAATTTGTGATGCTATTGCTTTATTTGTAACCATTATAAG
CTGCAATAAACAAGTTAACAACAACAATTGCATTCATTTTATGTTTCAGG
TTCAGGGGGAGGTGTGGGAGGTTTTTAAAGCAAGTAAAACCTCTACAAA
TGTGGTATGGAATTGGAGCCCCACTGTGTTCATCTTACAGATGGAAATAC
TGACATTCAGAGGAGTTAGTTAACTTGCCTAGGTGATTCAGCTAATAAGT
GCAAGAAAGATTTCAATCCAAGGTGATTTGATTCTGAAGCCTGTGCTAAT
CACATTACACCAAGCTACAACTTCATTTATAAATAATAAGTCAGCTTTCA
AGGGCCTTTCAGGTGTCCTGCACTTCTACAAGCTGTGCCATTTAGTGAAC
ACAAAATGAGCCTTCTGATGAAGTAGTCTTTTCATTATTTCAGATATTAG
AACACTAAAATTCTTAGCTGCCAGCTGATTGAAGGCTGGGACAAAATTCA
AACATGCATCTACAACAATATATATCTCAATGTTAGTCTCCAAATTCTAT
TGACTTCAACTCAAGAGAATATAAAGAGCTAGTCTTTATACACTCTTTAA
GGTATGATATCATCTGGAAAGTAACAAAATTGATGCAAATTTGAATGAAC
TTTATCATGGTGTATTTACACAATGTGTTTCTTCTCCCTGCAATGTATTT
CTTTCTCTAATTCCTTCCATTTGATCTTTCATACACAATCTGGTTCTGAT
GTATGTTTTTTGGATGCACTTTTCAACTCCAAAAGACAGAGCTAGTTACT
TTCTTCCTGGTGCTCCAAGCACTGTATTTGTATCTGTATTCAAGCCCTTT
GCAATATTGTACTGGATCATTATTTCACCTCTAGGATGGCTTCCCCAGGC
AACTTGTGTTCACCCAGAGACTACATTTGTATCTTGTTGACCTTTGAAC
TTCCACCAGTGTCTAAAAATAATATGTATGCAAAATTACTTGCTATGAGA
ATGTATAATTAAACAATATAAAAGGAGAAGCAAGGAGAGAAACACAGG
TGTGTATTTGTGTTTGTGTGCTTAAAAGGCAGTGTGGAAAAGGAAGAAAT
GCCATTTATAGTGAGGAGACAAAGTTATATTACCTCTTATCTGGCTTTTAA
GGAGATTTTGCTGAGCTAAAAATCCTATATTCATAGAAAAGCCTTACCTG
AGTTGCCAATACCTCAATTCTAAAATACAGCATAGCAAAACTTTAACCTC
CAAATCAAGCCTCTACTTGAATCCTTTTCTGAGGGATGAATAAGGCATAG
GCATCAGGGGCTGTTGCCAATGTGCATTAGCTGTTTGCAGCCTCACCTTC
TTTCATGGAGTTTAAGATATAGTGTATTTTCCCAAGGTTTGAACTAGCTC
TTCATTTCTTTATGTTTTAAATGCACTGACCTCCCACATTCCCTTTTTAG
TAAAATATTCAGAAATAATTTAAATACATCATTGCAATGAAAATAAATGT
TTTTTATTAGGCAGAATCCAGATGCTCAAGGCCCTTCATAATATCCCCCA
GTTAGTAGTTGGACTTAGGGAACAAAGGAACCTTTAATAGAAATTGGAC
AGCAAGAAAGCTCTAGCTTTAGAAGAACTCATCAAGAAGTCTGTAGAAGG
CAATTCTCTGGGAGTCAGGGGCTGCAATGCCATAGAGCACTAGGAACCTG
TCTGCCCACTCTCCCCCTAGCTCTTCTGCTATGTCCCTGGTTGCTAGGGC
AATGTCCTGGTACCTGTCAGCCACTCCCAGCCTGCCACAGTCTATGAAGC
CAGAGAACCTTCCATTTTCAACCATGATGTTGGGAAGGCAGGCATCCCCA
TGAGTCACCACTAGGTCCTCACCATCTGGCATGGATGCCTTGAGCCTGGC
AAATAGTTCAGCAGGGGCCAGGCCCTGGTGTTCTTCATCCAAGTCATCTT
GGTCCACCAGGCCAGCCTCCATCCTGGTTCTGGCCCTCTCTATCCTGTGC
TTGGCCTGGTGGTCAAAGGGGCAGGTGGCTGGGTCAAGGGTGTGGAGTCT
TCTCATGGCATCAGCCATGATTGACACTTTCTCAGCTGGAGCTAGGTGAG
AGGAAAGGAGGTCCTGCCCAGGCACCTCACCTAGTAGGAGCCAGTCCCTT

FIGURE 5 (cont.)

CCAGCTTCTGTGACCACATCAAGGACAGCTGCACAGGGGACCCCAGTTGT
TGCCAACCAGGAGAGTCTGGCAGCCTCATCCTGGAGCTCATTGAGAGCCC
CACTGAGGTCTGTCTTTACAAAAAGGACTGGCCTGCCTTGGGCTGAAAGT
CTGAAAACTGCTGCATCAGAGCAACCAATGGTCTGCTGTGCCCAGTCATA
GCCAAACAGTCTCTCAACCCAGGCAGCTGGAGAACCTGCATGTAGGCCAT
CTTGTTCAATCATGATGGCTCCTCCTGTCAGGAGAGGAAAGAGAAGAAGG
TTAGTACAATTGCTATAGTGAGTTGTATTATACTATGCTTATGATTAATT
GTCAAACTAGGGCTGCAGGGTTCATAGTGCCACTTTTCCTGCACTGCCCC
ATCTCCTGCCCACCCTTTCCCAGGCATAGACAGTCAGTGACTTACCAAAC
TCACAGGAGGGAGAAGGCAGAAGCTTTTTGCAAAAGCCTAGGCCTCCAAA
AAAGCCTCCTCACTACTTCTGGAATAGCTCAGAGGCCCAGGGGGCCTGGG
CCTCTGCATAAATAAAAAAAATTAGTCAGCCTGGGGCTGGGGTGGGGGCA
GGGGTGGGGGGCCAACTGGGCAGGGGTGGGGGGCCACTAGTGGGACTAT
GGTTGCTGACTAATTGAGATGCATGCTTTGCATACTTCTGCCTGCTGGGA
GCCTGGGGACTTTCCACACCTGGTTGCTGACTAATTGAGATGCATGCTTT
GCATACTTCTGCCTGCTGGGGAGCCTGGGGACTTTCCACACCCTAACTGA
CACACATTCCACAGCTGGTTCTTTCAGCCTCAGAAGGTACCTAACCAAGT
TCCTCTTTCAGAGGTTATTTCAGGCCCTGCAGGAATTCAGTCAATATGTT
CACCCCAAAAAAGCTGTTTGTTAACTTGTCAACCTCATTCTAAAATGTAT
ATAGAAGCCCAAAAGACAATAACAAAAATATTCTTGTAGAACAAAATGG
GAAAGAATGTTCCACTAAATATCAAGATTTAGAGCAAAGCATGAGATGTG
TGGGGATAGACAGTGAGGCTGATAAAATAGAGTAGAGCTCAGAAACAGA
CCCATTGATATATGTAAGTGACCTATGAAAAAAATATGGCATTTTACAAT
GGGAAAATGATGGTCTTTTCTTTTTAGAAAAACAGGGAAATATATTTAT
ATGTAAAAAATAAAAGGGAACCCATATGTCATACCATACACACAAAAAA
ATTCCAGTGAATTATAAGTCTAAATGGAGAAGGCAAAACTTTAAATCTTTT
AGAAAATAATATAGAAGCATGCCATCAAGACTTCAGTGTAGAGAAAAATT
TCTTATGACTCAAAGTCCTAACCACAAAGAAAAGATTGTTAATTAGATTG
CATGAATATTAAGACTTATTTTAAAATTAAAAAACCATTAAGAAAAGTC
AGGCCATAGAATGACAGAAAATATTTGCAACACCCCAGTAAAGAGAATTG
TAATATGCAGATTATAAAAGAAGTCTTACAAATCAGTAAAAAATAAAAC
TAGACAAAAATTTGAACAGATGAAAGAGAAACTCTAAATAATCATTACAC
ATGAGAAACTCAATCTCAGAAATCAGAGAACTATCATTGCATATACACTA
AATTAGAGAAATATTAAAAGGCTAAGTAACATCTGTGGCTTAATTAAGTT
ATCCTAGGAAACCTTAAAACCTTTAAAAGCCTTATATATTCTTTTTTTTCT
TATAAAACTTAAAACCTTAGAGGCTATTTAAGTTGCTGATTTATATTAAT
TTTATTGTTCAAACATGAGAGCTTAGTACATGAAACATGAGAGCTTAGTA
CATTAGCCATGAGAGCTTAGTACATTAGCCATGAGGGTTTAGTTCATTAA
ACATGAGAGCTTAGTACATTAAACATGAGAGCTTAGTACATACTATCAAC
AGGTTGAACTGCTGATT (SEQ ID NO. 4)

FIGURE 7 agatccgatTTTTCCCCGTATCCCCCCAGGTGTCTGCAGGCTCAAAGAGC
AGCGAGAAGCGTTCAGAGGAAAGCGATCCCGTGCCACCTTCCCCGTGCCC
GGGCTGTCCCCGCACGCTGCCGGCTCGGGGATGCGGGGGAGCGCCGGACC
GGACCGGAGCCCCGGGCGGCTCGCTGCTGCCCTAGCGGGGGAGGGACGT
AATTACATCCCTGGGGGCTTTGGGGGGGGGCTGTCCCactagaTTTTCCCC
GTATCCCCCCAGGTGTCTGCAGGCTCAAAGAGCAGCGAGAAGCGTTCAGA
GGAAAGCGATCCCGTGCCACCTTCCCCGTGCCCGGGCTGTCCCCGCACGC
TGCCGGCTCGGGGATGCGGGGGAGCGCCGGACCGGACCGGAGCCCCGGG
CGGCTCGCTGCTGCCCTAGCGGGGGAGGGACGTAATTACATCCCTGGGGG
CTTTGGGGGGGGGCTGTCCCatcggatctTCTAGAGAGTTCTTCTGTTTGC
TAGATAAGAAATCCTGGTCTGCCATCCCAGCAGGCCCAGGCTGTTTAAGT
TACTAGATAACAGGGTTGTTATTGATCCTATTATTATTATTTTTTCTACT
CTTCCTGATTCCCTGAAGTCCAAGGGACGTTTTTTTCTATTAAGAATGAT
TTTTTGTTTAAAAAAAAAAAAAGAGTCCTTGTTGTGTCGCTAGCTGGTCT
GTGACAGATAGAGCCCAGAGCTGCCTCAGTGCCCTTTACTCAGGAGTGGG
AGAACAGAAAGTAAATAAGCCAGAGCCCAGAGCACTCTTAGTCATCTGGA
TGGCTCAGCGCTGGGCCCAGCACTTGCAAATGCTGGCTCCTCCCGGACTC
CCCTGTTAGCCCCATGTTGTTAACCAGTTTAACATTCCCTTATCACATGC
TCATGTGGGCAGAATTAAGTGGAATTAGCTAACAAATTATATAAAATTCA
TTTACCTTTAAggatctACCAAATCAGGAACAGAAAGAGTCAAGGATCCC
CCAACCACTCCAAGTGGAGGCTGAGAAGGTTTTGTAGCTGGGTAGAGTA
TGTACTAAGAGATGGAGACAGCTGGCTCTGAGCTCTGAAGCAAGCACCTC
TTATGGAGAGTTGCTGACCTTCAGGTGCAAATCTAAGATACTACAGGAGA
ATACACCATgGGGCTTCAGCCCAGTTGACTCCCGAGTGGGCTATGGGTTT
GTGGAAGGAGAGATAGAAGAGAAGGGACCTTTCTTCTTGAATTCTGCTTT
CCTTCTACCTCTGAGGGTGAGCTGGGGTCTCAGCTGAGGTGAGGACACAG
CTATCAGTGGGAACTGTGAAACAACAGTTCAAGGGACAAAGTTACTAGGT
CCCCCAACAACTGCAGCCTCCTGGGGAATGATGTGGAAAAATGCTCAGCC
AAGGACAAAGAAGGCCTCACCCTCTCTGAGACAATGTCCCCTGCTGTGAA
CTGGTTCATCAGGCCACCCAGGAGCCCCTaTTAAGACTCTAATTACCCTA
AGGCTAAGTAGAGGTGTTGTTGTCCAATGAGCACTTTCTGCAGACCTAGC
ACCAGGCAAGTGTTTGGAAACTGCAGCTTCAGCCCCTCTGGCCATCTGCT
GATCCACCCTTAATGGGACAAACAGCAAAGTCCAGGGGTCAGGGGGGGG
TGCTTTGGACTATAAAGCTAGTGGGGATTCAGTAACCCCCAGCCCTAAGT
GACCAGCTACAGTCGGAAACCATCAGCAAGCAGGTATGTACTCTCCAGGG
TGGGCCTGGCTTCCCCAGTCAAGACTCCAGGGATTTGAGGGACGCTGTGG
GCTCTTCTCTTACATGTACCTTTTGCTAGCCTCAACCCTGACTATCTTCCA
GGTCATTGTTCCAACaagcttTATTGCGGTAGTTTATCACAGTTAAATTG
CTAACGCAGTCAGTGCTTCTGACACAACAGTCTCGAACTTAAGCTGCAGT
GACTCTCTTAAGGTAGCCTTGCAGAAGTTGGTCGTGAGGCACTGGGCAGG
TAAGTATCAAGGTTACAAGACAGGTTAAGGAGACCAATAGAAACTGGGC
TTGTCGAGACAGAGAAGACTCTTGCGTTCTGATAGGCACCTATTGGTCT
TACTGACATCCACTTTGCCTTTCTCTCCACAGGTGTCCACTCCCAGTTCA
ATTACAGCTCTTAAGGCTAGAGTACTTAATACGACTCACTATAGGCTAGC
CTCGAGAATTCACGCGTGGTACCTCTAGAgtcgacGGTATCGATAAGCTT
AGCCATGGCTTGCTCTGGATTCCGGAGCCATGGGGCTTGGCTGGAGCTTA
CTTCTAGGACCTGGCCCTGTACAGCTCTGTTTTCTCTTCTCTTCATCCCT

FIGURE 7 (cont.)

GTCTTCTCCAAAGGGATGCACGTGGCCCAACCTGCAGTAGTGCTGGCCAA
CAGCCGGGGTGTTGCCAGCTTTGTGTGTGAGTATGGGTCTGCAGGCAAAG
CTGCCGAGGTCCGGGTGACAGTGCTGCGGCGGGCCGGCAGCCAGATGACT
GAAGTCTGTGCCGCGACATATACTGTGGAGGATGAGTTGACCTTCCTTGA
TGACTCTACATGCACTGGCACCTCCACCGAAAACAAAGTGAACCTCACCA
TCCAAGGGCTGAGAGCCGTGGACACTGGGCTCTACATCTGCAAGGTGGAG
CTCCTGTACCCACCACCCTACTATGTGGGTATGGGCAACGGGACCCAGAT
TTATGTCATTGATCCAGAACCATGCCCAGATTCTGATGGTGGCTCCGGTG
GTGCTGCAGAGCCCAAATCTTGTGACAAAACTCACACATGCCCACCGTGC
CCAGGTAAGCCAGCCCAGGCCTCGCCCTCCAGCTCAAGGCGGGACAGGTG
CCCTAGAGTAGCCTGCATCCAGGGACAGGCCCCAGCCGGGTGCTGACACG
TCCACCTCCATCTCTTCCTCAGCACCTGAACTCCTGGGGGACCGTCAGT
CTTCCTCTTCCCCCCAAAACCCAAGGACACCCTCATGATCTCCCGGACCC
CTGAGGTCACATGCGTGGTGGTGGACGTGAGCCACGAAGACCCTGAGGTC
AAGTTCAACTGGTACGTGGACGGCGTGGAGGTGCATAATGCCAAGACAAA
GCCGCGGGAGGAGCAGTACAACAGCACGTACCGTGTGGTCAGCGTCCTCA
CCGTCCTGCACCAGGACTGGCTGAATGGCAAGGAGTACAAGTGCAAGGTC
TCCAACAAAGCCCTCCCAGCCCCATCGAGAAAACCATCTCCAAAGCCAA
AGGTGGGACCCGTGGGGTGCGAGGGCCACATGGACAGAGCCGGCTCGGC
CCACCCTCTGCCCTGGGAGTGACCGCTGTACCAACCTCTGTCCCTACAGGG
CAGCCCCGAGAACCACAGGTGTACACCCTGCCCCATCCCGGGATGAGCT
GACCAAGAACCAGGTCAGCCTGACCTGCCTGGTCAAAGGCTTCTATCCCA
GCGACATCGCCGTGGAGTGGGAGAGCAATGGGCAGCCGGAGAACAACTA
CAAGGCCACGCCTCCCGTGCTGGACTCCGACGGCTCCTTCTTCCTCTACAG
CAAGCTCACCGTGGACAAGAGCAGGTGGCAGCAGGGGAACGTCTTCTCAT
GCTCCGTGATGCATGAGGCTCTGCACAACCACTACACGCAGAAGAGCCTC
TCCCTGTCTCCGGGTAAATGAGTGCGACGGCCGGCAAGCCCCGCTCCCC
GGGCTCTCGCGGTCGCACGAGGATGCTTGGCACGTACCCCGTGTACATAC
TTCCCGGGCGCCCAGCATGGAAATAAAGCACCCAGCGCTGCCCTGGGCCC
CTGCGAGACTGTGATGGTTCTTTCCACGGGTCAGGCCGAGTCTGAGGCCT
GAGTGGCATGAGGGAGGCAgcggccgcTTCCCTTTAGTGAGGGTTAATGC
TTCGAGCAGACATGATAAGATACATTGATGAGTTTGGACAAACCACAACT
AGAATGCAGTGAAAAAAATGCTTTATTTGTGAAATTTGTGATGCTATTGC
TTTATTTGTAACCATTATAAGCTGCAATAAACAAGTTAACAACAACAATT
GCATTCATTTTATGTTTCAGGTTCAGGGGGAGATGTGGGAGGTTTTTTAA
AGCAAGTAAAACCTCTACAAATGTGGTAAAATCCGATAAGgatcgatTTT
TCCCCGTATCCCCCCAGGTGTCTGCAGGCTCAAAGAGCAGCGAGAAGCGT
TCAGAGGAAAGCGATCCCGTGCCACCTTCCCCGTGCCCGGGCTGTCCCCG
CACGCTGCCGGCTCGGGGATGCGGGGGAGCGCCGGACCGGACCGGAGCC
CCGGGCGGCTCGCTGCTGCCCTAGCGGGGGAGGGACGTAATTACATCCCT
GGGGGCTTTGGGGGGGGCTGTCCCactagaTTTTCCCCGTATCCCCCAG
GTGTCTGCAGGCTCAAAGAGCAGCGAGAAGCGTTCAGAGGAAAGCGATC
CCGTGCCACCTTCCCCGTGCCCGGGCTGTCCCCGCACGCTGCCGGCTCGGG
GATGCGGGGAGCGCCGGACCGGACCGGAGCCCGGGCGGCTCGCTGCT
GCCCTAGCGGGGAGGGACGTAATTACATCCCTGGGGGCTTTGGGGGGG
GCTGTCCCatcgatTTTTCCCCGTATCCCCCAGGTGTCTGCAGGCTCAAA
GAGCAGCGAGAAGCGTTCAGAGGAAAGCGATCCCGTGCCACCTTCCCCGT
GCCCGGGCTGTCCCCGCACGCTGCCGGCTCGGGGATGCGGGGAGCGCCG

FIGURE 7 (cont.)

GACCGGACCGGAGCCCCGGGCGGCTCGCTGCTGCCCTAGCGGGGGAGGG
ACGTAATTACATCCCTGGGGGCTTTGGGGGGGGGCTGTCCCactagaTTTT
CCCCGTATCCCCCAGGTGTCTGCAGGCTCAAAGAGCAGCGAGAAGCGTT
CAGAGGAAAGCGATCCCGTGCCACCTTCCCCGTGCCCGGGCTGTCCCCGC
ACGCTGCCGGCTCGGGGATGCGGGGGAGCGCCGGACCGGACCGGAGCCC
CGGGCGGCTCGCTGCTGCCCTAGCGGGGGAGGGACGTAATTACATCCCTG
GGGGCTTTGGGGGGGGCTGTCCCatcgatAGCGATAAGGATCCGCGTATG
GTGCACTCTCAGTACAATCTGCTCTGATGCCGCATAGTTAAGCCAGCCCC
GACACCCGCCAACACCCGCTGACGCGCCCTGACGGGCTTGTCTGCTCCG
GCATCCGCTTACAGACAAGCTGTGACCGTCTCCGGGAGCTGCATGTGTCA
GAGGTTTTCACCGTCATCACCGAAACGCGCGAGACGAAAGGGCCTCGTGA
TACGCCTATTTTATAGGTTAATGTCATGATAATAATGGTTTCTTAGACG
TCAGGTGGCACTTTTCGGGGAAATGTGCGCGGAACCCCTATTTGTTTATT
TTTCTAAATACATTCAAATATGTATCCGCTCATGAGACAATAACCCTGAT
AAATGCTTCAATAATATTGAAAAAGGAAGAGTATGAGTATTCAACATTTC
CGTGTCGCCCTTATTCCCTTTTTTGCGGCATTTTGCCTTCCTGTTTTTGC
TCACCCAGAAACGCTGGTGAAAGTAAAAGATGCTGAAGATCAGTTGGGTG
CACGAGTGGGTTACATCGAACTGGATCTCAACAGCGGTAAGATCCTTGAG
AGTTTTCGCCCCGAAGAACGTTTTCCAATGATGAGCACTTTTAAAGTTCT
GCTATGTGGCGCGGTATTATCCCGTATTGACGCCGGGCAAGAGCAACTCG
GTCGCCGCATACACTATTCTCAGAATGACTTGGTTGAGTACTCACCAGTC
ACAGAAAGCATCTTACGGATGGCATGACAGTAAGAGAATTATGCAGTGC
TGCCATAACCATGAGTGATAACACTGCGGCCAACTTACTTCTGACAACGA
TCGGAGGACCGAAGGAGCTAACCGCTTTTTTGCACAACATGGGGGATCAT
GTAACTCGCCTTGATCGTTGGGAACCGGAGCTGAATGAAGCCATACCAAA
CGACGAGCGTGACACCACGATGCCTGTAGCAATGGCAACAACGTTGCGCA
AACTATTAACTGGCGAACTACTTACTCTAGCTTCCCGGCAACAATTAATA
GACTGGATGGAGGCGGATAAAGTTGCAGGACCACTTCTGCGCTCGGCCCT
TCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATC
GTAGTTATCTACACGACGGGGAGTCAGGCAACTATGGATGAACGAAATAG
ACAGATCGCTGAGATAGGTGCCTCACTGATTAAGCATTGGTAACTGTCAG
ACCAAGTTTACTCATATATACTTTAGATTGATTTAAAACTTCATTTTTAA
TTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGA
TCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGA
GCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAAC
TCTGTAGCACCGCCTACATACCTCGCTCTGCTAATCCTGTTACCAGTGGC
TGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACA
CAGCCCAGCTTGGAGCGAACGACCTACACCGAACTGAGATACCTACAGCG
TGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTC
CAGGGGGAAACGCCTGGTATCTTTATAGTCCTGTCGGGTTTCGCCACCTCT
GACTTGAGCGTCGATTTTGTGATGCTCGTCAGGGGGCGGAGCCTATGG
AAAAACGCCAGCAACGCGGCCTTTTACGGTTCCTGGCCTTTTGCTGGCCT
TTTGCTCACATGGCTCGAC (SEQ ID NO. 5)

SEQUENCE LISTING

```
<160> NUMBER OF SEQ ID NOS: 11

<210> SEQ ID NO 1
<211> LENGTH: 223
<212> TYPE: PRT
<213> ORGANISM: Sus sp.

<400> SEQUENCE: 1

Met Ala Cys Ser Gly Phe Arg Ser His Gly Ala Trp Leu Glu Leu Thr
1               5                   10                  15

Ser Arg Thr Trp Pro Cys Thr Ala Leu Phe Ser Leu Leu Phe Ile Pro
            20                  25                  30

Val Phe Ser Lys Gly Met His Val Ala Gln Pro Ala Val Val Leu Ala
        35                  40                  45

Asn Ser Arg Gly Val Ala Ser Phe Val Cys Glu Tyr Gly Ser Ala Gly
    50                  55                  60
```

Lys Ala Glu Val Arg Val Thr Val Leu Arg Ala Gly Ser Gln
65              70                  75                  80

Met Thr Glu Val Cys Ala Ala Thr Tyr Thr Val Glu Asp Glu Leu Thr
                85                  90                  95

Phe Leu Asp Asp Ser Thr Cys Thr Gly Thr Ser Thr Glu Asn Lys Val
                100                 105                 110

Asn Leu Thr Ile Gln Gly Leu Arg Ala Val Asp Thr Gly Leu Tyr Ile
            115                 120                 125

Cys Lys Val Glu Leu Leu Tyr Pro Pro Tyr Val Gly Met Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Ile Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
210                 215                 220

<210> SEQ ID NO 2
<211> LENGTH: 672
<212> TYPE: DNA
<213> ORGANISM: Sus sp.

<400> SEQUENCE: 2
atggcttgct ctggattccg gagccatggg gcttggctgg agcttacttc taggacctgg      60
ccctgtacag ctctgttttc tcttctcttc atccctgtct tctccaaagg gatgcacgtg     120
gcccaacctg cagtagtgct ggccaacagc cggggtgttg ccagctttgt gtgtgagtat     180
gggtctgcag gcaaagctgc cgaggtccgg gtgacagtgc tgcggcgggc cggcagccag     240
atgactgaag tctgtgccgc gacatatact gtggaggatg agttgacctt ccttgatgac     300
tctacatgca ctggcacctc caccgaaaac aaagtgaacc tcaccatcca agggctgaga     360
gccgtggaca ctgggctcta catctgcaag gtggagctcc tgtacccacc ccctactat     420 gtgggtatgg gcaacgggac ccagatttat gtcattgatc cagaaccatg cccagattct     480
gatttcctgc tctggatcct ggcagcagtt agttcagggt tgttttttta cagcttcctc     540
atcacagctg tttcttttgag caaaatgcta aagaaaagaa gtcctcttac tacaggggtc     600
tatgtgaaaa tgcccccgac agagccagaa tgtgaaaagc aatttcagcc ttatttttatt     660 cccatcaatt ga                                                          672

<210> SEQ ID NO 3
<211> LENGTH: 400
<212> TYPE: PRT
<213> ORGANISM: Sus sp.

<400> SEQUENCE: 3

Met Ala Cys Ser Gly Phe Arg Ser His Gly Ala Trp Leu Glu Leu Thr
1               5                   10                  15

Ser Arg Thr Trp Pro Cys Thr Ala Leu Phe Ser Leu Leu Phe Ile Pro
            20                  25                  30

Val Phe Ser Lys Gly Met His Val Ala Gln Pro Ala Val Val Leu Ala
        35                  40                  45

```
Asn Ser Arg Gly Val Ala Ser Phe Val Cys Glu Tyr Gly Ser Ala Gly
         50                  55                  60
Lys Ala Ala Glu Val Arg Val Thr Val Leu Arg Arg Ala Gly Ser Gln
 65                  70                  75                  80
Met Thr Glu Val Cys Ala Ala Thr Tyr Thr Val Glu Asp Glu Leu Thr
                 85                  90                  95
Phe Leu Asp Asp Ser Thr Cys Thr Gly Thr Ser Thr Glu Asn Lys Val
                100                 105                 110
Asn Leu Thr Ile Gln Gly Leu Arg Ala Val Asp Thr Gly Leu Tyr Ile
            115                 120                 125
Cys Lys Val Glu Leu Leu Tyr Pro Pro Tyr Tyr Val Gly Met Gly
130                 135                 140
Asn Gly Thr Gln Ile Tyr Val Ile Asp Pro Glu Pro Cys Pro Asp Ser
145                 150                 155                 160
Asp Gly Gly Ser Gly Gly Ala Ala Glu Pro Lys Ser Cys Asp Lys Thr
                165                 170                 175
His Thr Cys Pro Pro Cys Pro Ala Pro Glu Leu Leu Gly Gly Pro Ser
                180                 185                 190
Val Phe Leu Phe Pro Pro Lys Pro Lys Thr Asp Leu Met Ile Ser Arg
            195                 200                 205
Thr Pro Glu Val Thr Cys Val Val Val Asp Val Ser His Glu Asp Pro
210                 215                 220
Glu Val Lys Phe Asn Trp Tyr Val Asp Gly Val Glu Val His Asn Ala
225                 230                 235                 240
Lys Thr Lys Pro Arg Glu Glu Gln Tyr Asn Ser Thr Tyr Arg Val Val
                245                 250                 255
Ser Val Leu Thr Val Leu His Gln Asp Trp Leu Asn Gly Lys Glu Tyr
                260                 265                 270
Lys Cys Lys Val Ser Asn Lys Ala Leu Pro Ala Pro Ile Glu Lys Thr
            275                 280                 285
Ile Ser Lys Ala Lys Gly Gln Pro Arg Glu Pro Gln Val Tyr Thr Leu
290                 295                 300
Pro Pro Ser Arg Asp Glu Leu Thr Lys Asn Gln Val Ser Leu Thr Cys
305                 310                 315                 320
Leu Val Lys Gly Phe Tyr Pro Ser Asp Ile Ala Val Glu Trp Glu Ser
                325                 330                 335
Asn Gly Gln Pro Glu Asn Asn Tyr Lys Thr Thr Pro Pro Val Leu Asp
                340                 345                 350
Ser Asp Gly Ser Phe Phe Leu Tyr Ser Lys Leu Thr Val Asp Lys Ser
            355                 360                 365
Arg Trp Gln Gln Gly Asn Val Phe Ser Cys Ser Val Met His Glu Ala
370                 375                 380
Leu His Asn His Tyr Thr Gln Lys Ser Leu Ser Leu Ser Pro Gly Lys
385                 390                 395                 400

<210> SEQ ID NO 4
<211> LENGTH: 8767
<212> TYPE: DNA
<213> ORGANISM: Artificial Sequence
<220> FEATURE:
<223> OTHER INFORMATION: Synthetic

<400> SEQUENCE: 4
ttaattaaaa ttatctctaa ggcatgtgaa ctggctgtct tggttttcat ctgtacttca    60
tctgctacct ctgtgacctg aaacatattt ataattccat taagctgtgc atatgataga   120
```

```
tttatcatat gtattttcct taaaggattt ttgtaagaac taattgaatt gatacctgta    180
aagtctttat cacactaccc aataaataat aaatctcttt gttcagctct ctgtttctat    240
aaatatgtac aagttttatt gtttttagtg gtagtgattt tattctcttt ctatatatat    300
acacacacat gtgtgcattc ataaatatat acaatttttta tgaataaaaa attattagca    360
atcaatattg aaaccactg attttttgttt atgtgagcaa acagcagatt aaaaggaatt    420
cctgcaggag tcaatgggaa aacccattg gagccaagta cactgactca atagggactt    480
tccattgggt tttgcccagt acataaggtc aatagggggt gagtcaacag gaaagtccca    540
ttggagccaa gtacattgag tcaataggga cttttccaatg ggttttgccc agtacataag    600
gtcaatggga ggtaagccaa tgggttttttc ccattactga catgtatacg cgtcgacgtc    660
ggcgcgttca gcctaaagct tttttccccg tatcccccca ggtgtctgca ggctcaaaga    720
gcagcgagaa gcgttcagag gaaagcgatc ccgtgccacc ttccccgtgc ccgggctgtc    780
cccgcacgct gccggctcgg ggatgcgggg gagcgccgga ccggaccgga gccccgggcg    840
gctcgctgct gccctagcgg gggagggacg taattacatc cctgggggct ttgggggggg    900
gctgtccctg cggccgcgaa ttcgtaatca tggtcatagc tgtttcctgt gtgaaattgt    960
tatccgctca caattccaca caacatacga gccggaagca taaagtgtaa agcctggggt   1020
gcctaatgag tgagctaact cacattaatt gcgttgcgct cactgcccgc tttccagtcg   1080
ggaaacctgt cgtgccaggg gtctagccgc ggtctaggaa gctttctagg gtacctctag   1140
ggatccacta gttattaata gtaatcaatt acggggtcat tagttcatag cccatatatg   1200
gagttccgcg ttacataact tacggtaaat ggcccgcctg gctgaccgcc caacgacccc   1260
cgcccattga cgtcaataat gacgtatgtt cccatagtaa cgccaatagg gactttccat   1320
tgacgtcaat gggtggagta tttacggtaa actgcccact tggcagtaca tcaagtgtat   1380
catatgccaa gtacgccccc tattgacgtc aatgacggta atggcccgc ctggcattat    1440 gcccagtaca tgaccttatg gactttcct acttggcagt acatctacgt attagtcatc   1500
gctattacca tgggtcgagg tgagccccac gttctgcttc actctcccca tctccccccc   1560
ctccccaccc ccaattttgt atttatttat ttttaatta ttttgtgcag cgatgggggc   1620
gggggggggg gggcgcgcg ccaggcgggg cggggcgggg cgaggggcgg ggcggggcga   1680
ggcggagagg tgcggcggca gccaatcaga gcggcgcgct ccgaaagttt ccttttatgg   1740
cgaggcggcg gcggcggcgg ccctataaaa agcgaagcgc gcggcgggcg ggagtcgctg   1800
cgttgccttc gccccgtgcc ccgctccgcg ccgcctcgcg ccgcccgccc cggctctgac   1860
tgaccgcgtt actcccacag gtgagcgggc gggacggccc ttctcctccg ggctgtaatt   1920
agcgcttggt ttaatgacgg ctcgtttctt ttctgtggct gcgtgaaagc cttaaagggc   1980
tccgggaggg ccctttgtgc ggggggggagc ggctcggggg gtgcgtgcgt gtgtgtgtgc   2040
gtggggagcg ccgcgtgcgg cccgcgctgc ccggcggctg tgagcgctgc gggcgcggcg   2100
cggggctttg tgcgctccgc gtgtgcgcga ggggagcgcg gccggggggcg gtgccccgcg   2160 gtgcgggggg gctgcgaggg gaacaaaggc tgcgtgcggg gtgtgtgcgt ggggggggtga   2220 gcaggggggtg tgggcgcggc ggtcgggctg taaccccccc ctgcacccccc ctccccgagt   2280 tgctgagcac ggcccggctt cgggtgcggg gctccgtgcg gggcgtggcg cggggctcgc   2340
cgtgccgggc gggggggtggc ggcaggtggg ggtgccgggc ggggcgggc cgcctcgggc   2400 cgggggaggggc tcgggggagg ggcgcggcgg ccccggagcg ccggcggctg tcgaggcgcg   2460
```

```
gcgagccgca gccattgcct tttatggtaa tcgtgcgaga gggcgcaggg acttcctttg   2520
tcccaaatct ggcggagccg aaatctggga ggcgccgccg cacccctct agcgggcgcg    2580 ggcgaagcgg tgcggcgccg gcaggaagga aatgggcggg gagggccttc gtgcgtcgcc   2640
gcgccgccgt ccccttctcc atctccagcc tcggggctgc cgcagggga cggctgcctt    2700 cggggggggac ggggcagggc ggggttcggc ttctggcgtg tgaccggcgg ctctagagcc  2760
tctgctaacc atgttcatgc cttcttcttt ttcctacagc tcctgggcaa cgtgctggtt   2820
gttgtgctgt ctcatcattt tggcaaagaa ttccgctgcg actcggcgga gtcccggcgg   2880
cgcgtccttg ttctaacccg gcgcgtggta cctctagagt cgacggtatc gataagctta   2940
gccatggctt gctctggatt ccggagccat ggggcttggc tggagcttac ttctaggacc   3000
tggccctgta cagctctgtt ttctcttctc ttcatccctg tcttctccaa agggatgcac   3060
gtggcccaac ctgcagtagt gctggccaac agccggggtg ttgccagctt tgtgtgtgag   3120
tatgggtctg caggcaaagc tgccgaggtc cgggtgacag tgctgcggcg ggccggcagc   3180
cagatgactg aagtctgtgc cgcgacatat actgtggagg atgagttgac cttccttgat   3240
gactctacat gcactggcac ctccaccgaa aacaaagtga acctcaccat ccaagggctg   3300
agagccgtgg acactgggct ctacatctgc aaggtggagc tcctgtaccc accacctac    3360 tatgtgggta tgggcaacgg gacccagatt tatgtcattg atccagaacc atgcccagat   3420
tctgatggtg gctccggtgg tgctgcagag cccaaatctt gtgacaaaac tcacacatgc   3480
ccaccgtgcc caggtaagcc agcccaggcc tcgcctcca gctcaaggcg gacaggtgc     3540 cctagagtag cctgcatcca gggacaggcc ccagccgggt gctgacacgt ccacctccat   3600
ctcttcctca gcacctgaac tcctgggggg accgtcagtc ttcctcttcc ccccaaaacc   3660
caaggacacc ctcatgatct cccggacccc tgaggtcaca tgcgtggtgg tggacgtgag   3720
ccacgaagac cctgaggtca gttcaactg gtacgtggac ggcgtggagg tgcataatgc    3780
caagacaaag ccgcgggagg agcagtacaa cagcacgtac cgtgtggtca gcgtcctcac   3840
cgtcctgcac caggactggc tgaatggcaa ggagtacaag tgcaaggtct ccaacaaagc   3900
cctcccagcc cccatcgaga aaaccatctc caaagccaaa ggtgggaccc gtggggtgcg   3960
agggccacat ggacagagcc ggctcggccc accctctgcc ctgggagtga ccgctgtacc   4020
aacctctgtc cctacagggc agccccgaga accacaggtg tacaccctgc ccccatcccg   4080
ggatgagctg accaagaacc aggtcagcct gacctgcctg gtcaaaggct tctatcccag   4140
cgacatcgcc gtggagtggg agagcaatgg gcagccggag aacaactaca aggccacgcc   4200
tcccgtgctg gactccgacg gctccttctt cctctacagc aagctcaccg tggacaagag   4260
caggtggcag caggggaacg tcttctcatg ctccgtgatg catgaggctc tgcacaacca   4320
ctacacgcag aagagcctct ccctgtctcc gggtaaatga gtgcgacggc cggcaagccc   4380
ccgctccccg ggctctcgcg gtcgcacgag gatgcttggc acgtaccccg tgtacatact   4440
tcccgggcgc ccagcatgga aataaagcac ccagcgctgc cctgggcccc tgcgagactg   4500
tgatggttct ttccacgggt caggccgagt ctgaggcctg agtggcatga gggaggcagc   4560
ggccgccata tgcatcctag ctggccagac atgataagat acattgatga gtttggacaa   4620
accacaacta gaatgcagtg aaaaaaatgc tttatttgtg aaatttgtga tgctattgct   4680
ttatttgtaa ccattataag ctgcaataaa caagttaaca acaacaattg cattcatttt   4740
atgtttcagg ttcaggggga ggtgtgggag gttttttaaa gcaagtaaaa cctctacaaa   4800
tgtggtatgg aattggagcc ccactgtgtt catcttacag atggaaatac tgacattcag   4860
```

```
aggagttagt taacttgcct aggtgattca gctaataagt gcaagaaaga tttcaatcca    4920
aggtgatttg attctgaagc ctgtgctaat cacattacac caagctacaa cttcatttat    4980
aaataataag tcagctttca agggcctttc aggtgtcctg cacttctaca agctgtgcca    5040
tttagtgaac acaaaatgag ccttctgatg aagtagtctt ttcattattt cagatattag    5100
aacactaaaa ttcttagctg ccagctgatt gaaggctggg acaaaattca aacatgcatc    5160
tacaacaata tatatctcaa tgttagtctc caaattctat tgacttcaac tcaagagaat    5220
ataaagagct agtctttata cactcttttaa ggtatgatat catctggaaa gtaacaaaat    5280
tgatgcaaat ttgaatgaac tttatcatgg tgtatttaca caatgtgttt cttctccctg    5340
caatgtattt ctttctctaa ttccttccat ttgatctttc atacacaatc tggttctgat    5400
gtatgttttt tggatgcact tttcaactcc aaaagacaga gctagttact ttcttcctgg    5460
tgctccaagc actgtatttg tatctgtatt caagcccttt gcaatattgt actggatcat    5520
tatttcacct ctaggatggc ttccccaggc aacttgtgtt cacccagaga ctacattttg    5580
tatcttgttg acctttgaac ttccaccagt gtctaaaaat aatatgtatg caaaattact    5640
tgctatgaga atgtataatt aaacaatata aaaaggagaa gcaaggagag aaacacaggt    5700
gtgtatttgt gtttgtgtgc ttaaaaggca gtgtggaaaa ggaagaaatg ccatttatag    5760
tgaggagaca aagttatatt acctcttatc tggcttttaa ggagattttg ctgagctaaa    5820
aatcctatat tcatagaaaa gccttacctg agttgccaat acctcaattc taaaatacag    5880
catagcaaaa ctttaacctc caaatcaagc ctctacttga atccttttct gagggatgaa    5940
taaggcatag gcatcagggg ctgttgccaa tgtgcattag ctgtttgcag cctcaccttc    6000
tttcatggag tttaagatat agtgtatttt cccaaggttt gaactagctc ttcatttctt    6060
tatgttttaa atgcactgac ctcccacatt cccttttttag taaaatattc agaaataatt    6120
taaatacatc attgcaatga aaataaatgt tttttattag gcagaatcca gatgctcaag    6180
gcccttcata atatccccca gtttagtagt tggacttagg gaacaaagga accttttaata    6240 gaaattggac agcaagaaag ctctagcttt agaagaactc atcaagaagt ctgtagaagg    6300
caattctctg ggagtcaggg gctgcaatgc catagagcac taggaacctg tctgcccact    6360
ctccccctag ctcttctgct atgtccctgg ttgctagggc aatgtcctgg tacctgtcag    6420
ccactcccag cctgccacag tctatgaagc cagagaacct tccatttca accatgatgt    6480 tgggaaggca ggcatcccca tgagtcacca ctaggtcctc accatctggc atggatgcct    6540
tgagcctggc aaatagttca gcaggggcca ggccctggtg ttcttcatcc aagtcatctc    6600
ggtccaccag gccagcctcc atcctggttc tggccctctc tatcctgtgc ttggcctggt    6660
ggtcaaaggg gcaggtggct gggtcaaggg tgtggagtct tctcatggca tcagccatga    6720 ttgacactttt ctcagctgga gctaggtgag aggaaaggag gtcctgccca ggcacctcac    6780
ctagtaggag ccagtccctt ccagcttctg tgaccacatc aaggacagct gcacagggga    6840
ccccagttgt tgccaaccag gagagtctgg cagcctcatc ctggagctca ttgagagccc    6900
cactgaggtc tgtctttaca aaaggactg gcctgccttg ggctgaaagt ctgaaaactg    6960
ctgcatcaga gcaaccaatg gtctgctgtg cccagtcata gccaaacagt ctctcaaccc    7020
aggcagctgg agaacctgca tgtaggccat cttgttcaat catgatggct cctcctgtca    7080
ggagaggaaa gagaagaagg ttagtacaat tgctatagtg agttgtatta tactatgctt    7140
atgattaatt gtcaaactag ggctgcaggg ttcatagtgc cacttttcct gcactgcccc    7200
```

```
atctcctgcc cacccttttcc caggcataga cagtcagtga cttaccaaac tcacaggagg    7260
gagaaggcag aagcttttttg caaaagccta ggcctccaaa aaagcctcct cactacttct    7320
ggaatagctc agaggcccag ggggcctggg cctctgcata aataaaaaaa attagtcagc    7380
ctggggctgg ggtgggggca ggggtggggg gccaactggg caggggtggg gggccactag    7440
tgggactatg gttgctgact aattgagatg catgctttgc atacttctgc ctgctgggga    7500
gcctggggac tttccacacc tggttgctga ctaattgaga tgcatgcttt gcatacttct    7560
gcctgctggg gagcctgggg actttccaca ccctaactga cacacattcc acagctggtt    7620
cttttcagcct cagaaggtac ctaaccaagt tcctctttca gaggttatttt caggccctgc    7680
aggaattcag tcaatatgtt caccccaaaa aagctgtttg ttaacttgtc aacctcattc    7740
taaaatgtat atagaagccc aaaagacaat aacaaaaata ttcttgtaga acaaatggg    7800
aaagaatgtt ccactaaata tcaagattta gagcaaagca tgagatgtgt ggggatagac    7860
agtgaggctg ataaaataga gtagagctca gaaacagacc cattgatata tgtaagtgac    7920
ctatgaaaaa aatatggcat tttacaatgg gaaaatgatg gtcttttttct tttttagaaa    7980
aacagggaaa tatatttata tgtaaaaaat aaaagggaac ccatatgtca taccatacac    8040
acaaaaaaat tccagtgaat tataagtcta aatggagaag gcaaaacttt aaatctttta    8100
gaaaataata tagaagcatg ccatcaagac ttcagtgtag agaaaaattt cttatgactc    8160
aaagtcctaa ccacaagaa aagattgtta attgagattgc atgaatatta agacttattt    8220
ttaaaattaa aaaccatta agaaaagtca ggccatagaa tgacagaaaa tatttgcaac    8280
accccagtaa agagaattgt aatatgcaga ttataaaaag aagtcttaca aatcagtaaa    8340
aaataaaact agacaaaaat ttgaacagat gaaagagaaa ctctaaataa tcattacaca    8400
tgagaaactc aatctcagaa atcagagaac tatcattgca tatacactaa attagagaaa    8460
tattaaaagg ctaagtaaca tctgtggctt aattaagtta tcctaggaaa ccttaaaacc    8520
tttaaaagcc ttatatattc tttttttttct tataaaactt aaaaccttag aggctattta    8580
agttgctgat ttatattaat tttattgttc aaacatgaga gcttagtaca tgaaacatga    8640
gagcttagta cattagccat gagagcttag tacattagcc atgagggttt agttcattaa    8700
acatgagagc ttagtacatt aaacatgaga gcttagtaca tactatcaac aggttgaact    8760
gctgatt                                                              8767

<210> SEQ ID NO 5
<211> LENGTH: 7169
<212> TYPE: DNA
<213> ORGANISM: Artificial Sequence
<220> FEATURE:
<223> OTHER INFORMATION: Synthetic

<400> SEQUENCE: 5
agatccgatt tttccccgta tcccccccagg tgtctgcagg ctcaaagagc agcgagaagc      60
gttcagagga aagcgatccc gtgccacctt ccccgtgccc gggctgtccc cgcacgctgc     120
cggctcgggg atgcggggga gcgccggacc ggaccggagc cccgggcggc tcgctgctgc     180
cctagcgggg gagggacgta attacatccc tgggggcttt ggggggggc tgtcccacta     240
gattttcccc gtatccccc aggtgtctgc aggctcaaag agcagcgaga agcgttcaga     300
ggaaagcgat cccgtgccac cttccccgtg cccgggctgt cccgcacgc tgccggctcg     360
gggatgcggg ggagcgccgg accggaccgg agccccgggc ggctcgctgc tgccctagcg     420
ggggagggac gtaattacat ccctgggggc tttgggggg ggctgtccca tcggatcttc     480
```

```
tagagagttc ttctgtttgc tagataagaa atcctggtct gccatcccag caggcccagg      540
ctgtttaagt tactagataa cagggttgtt attgatccta ttattattat tttttctact      600
cttcctgatt ccctgaagtc caagggacgt tttttttctat taagaatgat tttttgttta     660
aaaaaaaaaa aagagtcctt gttgtgtcgc tagctggtct gtgacagata gagcccagag      720
ctgcctcagt gcccttttact caggagtggg agaacagaaa gtaaataagc cagagcccag     780
agcactctta gtcatctgga tggctcagcg ctgggcccag cacttgcaaa tgctggctcc      840
tcccggactc ccctgttagc cccatgttgt taaccagttt aacattccct tatcacatgc      900
tcatgtgggc agaattaagt ggaattagct aacaaattat ataaaattca tttacctta      960 aggatctacc aaatcaggaa cagaaagagt caaggatccc ccaaccactc caagtggagg     1020
ctgagaaagg ttttgtagct gggtagagta tgtactaaga gatggagaca gctggctctg     1080
agctctgaag caagcacctc ttatggagag ttgctgacct tcaggtgcaa atctaagata     1140
ctacaggaga atacaccatg gggcttcagc ccagttgact cccgagtggg ctatgggttt     1200
gtggaaggag agatagaaga gaagggacct ttcttcttga attctgcttt ccttctacct     1260
ctgagggtga gctggggtct cagctgaggt gaggacacag ctatcagtgg gaactgtgaa     1320
acaacagttc aagggacaaa gttactaggt cccccaacaa ctgcagcctc ctggggaatg     1380
atgtggaaaa atgctcagcc aaggacaaag aaggcctcac cctctctgag acaatgtccc     1440
ctgctgtgaa ctggttcatc aggccaccca ggagcccta ttaagactct aattaccta      1500 aggctaagta gaggtgttgt tgtccaatga gcactttctg cagacctagc accaggcaag     1560
tgtttggaaa ctgcagcttc agcccctctg gccatctgct gatccaccct taatgggaca     1620
aacagcaaag tccaggggtc agggggggt gctttggact ataaagctag tggggattca     1680
gtaaccccca gccctaagtg accagctaca gtcggaaacc atcagcaagc aggtatgtac     1740
tctccagggt gggcctggct tccccagtca agactccagg gatttgaggg acgctgtggg     1800
ctcttctctt acatgtacct tttgctagcc tcaaccctga ctatcttcca ggtcattgtt     1860
ccaacaagct ttattgcggt agtttatcac agttaaattg ctaacgcagt cagtgcttct     1920
gacacaacag tctcgaactt aagctgcagt gactctctta aggtagcctt gcagaagttg     1980
gtcgtgaggc actgggcagg taagtatcaa ggttacaaga caggtttaag gagaccaata     2040
gaaactgggc ttgtcgagac agagaagact cttgcgtttc tgataggcac ctattggtct     2100
tactgacatc cactttgcct ttctctccac aggtgtccac tcccagttca attacagctc     2160
ttaaggctag agtacttaat acgactcact ataggctagc ctcgagaatt cacgcgtggt     2220
acctctagag tcgacggtat cgataagctt agccatggct tgctctggat tccggagcca     2280
tggggcttgg ctggagctta cttctaggac ctggccctgt acagctctgt tttctcttct     2340
cttcatccct gtcttctcca aagggatgca cgtggcccaa cctgcagtag tgctggccaa     2400
cagccggggt gttgccagct ttgtgtgtga gtatgggtct gcaggcaaag ctgccgaggt     2460
ccgggtgaca gtgctgcggc gggccggcag ccagatgact gaagtctgtg ccgcgacata     2520
tactgtggag gatgagttga ccttccttga tgactctaca tgcactggca cctccaccga     2580
aaacaaagtg aacctcacca tccaagggct gagagccgtg gacactgggc tctacatctg     2640
caaggtggag ctcctgtacc caccacccta ctatgtgggt atgggcaacg gacccagat     2700 ttatgtcatt gatccagaac catgcccaga ttctgatggt ggctccggtg gtgctgcaga     2760
gcccaaatct tgtgacaaaa ctcacacatg cccaccgtgc ccaggtaagc cagcccaggc     2820
```

-continued

```
ctcgccctcc agctcaaggc gggacaggtg ccctagagta gcctgcatcc agggacaggc    2880
cccagccggg tgctgacacg tccacctcca tctcttcctc agcacctgaa ctcctgggg     2940 gaccgtcagt cttcctcttc cccccaaaac ccaaggacac cctcatgatc tcccggaccc    3000
ctgaggtcac atgcgtggtg gtggacgtga gccacgaaga ccctgaggtc aagttcaact    3060
ggtacgtgga cggcgtggag gtgcataatg ccaagacaaa gccgcgggag gagcagtaca    3120
acagcacgta ccgtgtggtc agcgtcctca ccgtcctgca ccaggactgg ctgaatggca    3180
aggagtacaa gtgcaaggtc tccaacaaag ccctcccagc cccatcgag aaaaccatct     3240 ccaaagccaa aggtgggacc cgtggggtgc gagggccaca tggacagagc cggctcggcc    3300
caccctctgc cctgggagtg accgctgtac caacctctgt ccctacaggg cagccccgag    3360
aaccacaggt gtacaccctg cccccatccc gggatgagct gaccaagaac caggtcagcc    3420
tgacctgcct ggtcaaaggc ttctatccca gcgacatcgc cgtggagtgg gagagcaatg    3480
ggcagccgga gaacaactac aaggccacgc ctcccgtgct ggactccgac ggctccttct    3540
tcctctacag caagctcacc gtggacaaga gcaggtggca gcagggaac gtcttctcat      3600 gctccgtgat gcatgaggct ctgcacaacc actacacgca gaagagcctc tccctgtctc    3660
cgggtaaatg agtgcgacgg ccggcaagcc cccgctcccc gggctctcgc ggtcgcacga    3720
ggatgcttgg cacgtacccc gtgtacatac ttcccgggcg cccagcatgg aaataaagca    3780
cccagcgctg ccctgggccc ctgcgagact gtgatggttc tttccacggg tcaggccgag    3840
tctgaggcct gagtggcatg agggaggcag cggccgcttc cctttagtga gggttaatgc    3900
ttcgagcaga catgataaga tacattgatga gtttggaca aaccacaact agaatgcagt    3960
gaaaaaaatg ctttatttgt gaaatttgtg atgctattgc tttatttgta accattataa    4020
gctgcaataa acaagttaac aacaacaatt gcattcattt tatgtttcag gttcaggggg    4080
agatgtggga ggttttttaa agcaagtaaa acctctacaa atgtggtaaa atccgataag    4140
gatcgatttt tccccgtatc cccccaggtg tctgcaggct caaagagcag cgagaagcgt    4200
tcagaggaaa gcgatcccgt gccaccttcc ccgtgcccgg gctgtccccg cacgctgccg    4260
gctcggggat gcggggagc gccggaccgg accggagccc cggcggctc gctgctgccc      4320 tagcggggga gggacgtaat tacatccctg ggggctttgg ggggggctg tcccactaga     4380 ttttccccgt atccccccag gtgtctgcag gctcaaagag cagcgagaag cgttcagagg    4440
aaagcgatcc cgtgccacct tccccgtgcc cgggctgtcc ccgcacgctg ccggctcggg    4500
gatgcggggg agcgccggac cggaccgag ccccgggcgg ctcgctgctg ccctagcggg     4560
ggagggacgt aattacatcc ctgggggctt tgggggggg ctgtcccatc gattttccc      4620 cgtatccccc caggtgtctg caggctcaaa gagcagcgag aagcgttcag aggaaagcga    4680
tcccgtgcca ccttccccgt gcccgggctg tccccgcacg ctgccggctc ggggatgcgg    4740
gggagcgccg gaccggaccg gagccccggg cggctcgctg ctgccctagc ggggaggga    4800 cgtaattaca tccctggggg ctttgggggg gggctgtccc actagatttt ccccgtatcc    4860
ccccaggtgt ctgcaggctc aaagagcagc gagaagcgtt cagaggaaag cgatcccgtg    4920
ccaccttccc cgtgcccggg ctgtccccgc acgctgccgg ctcggggatg cggggagcg     4980 ccggaccgga ccggagcccc gggcggctcg ctgctgccct agcggggag ggacgtaatt      5040 acatccctgg gggctttggg ggggctgt cccatcgata gcgataagga tccgcgtatg       5100
gtgcactctc agtacaatct gctctgatgc cgcatagtta agccagcccc gacacccgcc    5160
aacacccgct gacgcgccct gacgggcttg tctgctcccg gcatccgctt acagacaagc    5220
```

```
tgtgaccgtc tccgggagct gcatgtgtca gaggttttca ccgtcatcac cgaaacgcgc    5280
gagacgaaag ggcctcgtga tacgcctatt tttataggtt aatgtcatga taataatggt    5340
ttcttagacg tcaggtggca cttttcgggg aaatgtgcgc ggaacccta tttgtttatt    5400 tttctaaata cattcaaata tgtatccgct catgagacaa taaccctgat aaatgcttca    5460
ataatattga aaaggaaga gtatgagtat tcaacatttc cgtgtcgccc ttattccctt    5520
ttttgcggca ttttgccttc ctgttttgc tcacccagaa acgctggtga agtaaaaga    5580 tgctgaagat cagttgggtg cacgagtggg ttacatcgaa ctggatctca acagcggtaa    5640
gatccttgag agttttcgcc ccgaagaacg ttttccaatg atgagcactt ttaaagttct    5700
gctatgtggc gcggtattat cccgtattga cgccgggcaa gagcaactcg gtcgccgcat    5760
acactattct cagaatgact tggttgagta ctcaccagtc acagaaaagc atcttacgga    5820
tggcatgaca gtaagagaat tatgcagtgc tgccataacc atgagtgata acactgcggc    5880
caacttactt ctgacaacga tcggaggacc gaaggagcta accgcttttt tgcacaacat    5940
gggggatcat gtaactcgcc ttgatcgttg gaaccggag ctgaatgaag ccataccaaa    6000
cgacgagcgt gacaccacga tgcctgtagc aatggcaaca acgttgcgca aactattaac    6060
tggcgaacta cttactctag cttcccggca acaattaata gactggatgg aggcggataa    6120
agttgcagga ccacttctgc gctcggccct tccggctggc tggtttattg ctgataaatc    6180
tggagccggt gagcgtgggt ctcgcggtat cattgcagca ctggggccag atggtaagcc    6240
ctcccgtatc gtagttatct acacgacggg gagtcaggca actatggatg aacgaaatag    6300
acagatcgct gagataggtg cctcactgat taagcattgg taactgtcag accaagttta    6360
ctcatatata ctttagattg atttaaaact tcattttaa tttaaaagga tctaggtgaa    6420
gatccttttt gataatctca tgaccaaaat cccttaacgt gagttttcgt tccactgagc    6480
gtcagacccc gtagaaaaga tcaaaggatc ttcttgagat ccttttttc tgcgcgtaat    6540 ctgctgcttg caaacaaaaa aaccaccgct accagcggtg gtttgtttgc cggatcaaga    6600
gctaccaact cttttttccga aggtaactgg cttcagcaga gcgcagatac caaatactgt    6660
tcttctagtg tagccgtagt taggccacca cttcaagaac tctgtagcac cgcctacata    6720
cctcgctctg ctaatcctgt taccagtggc tgctgccagt ggcgataagt cgtgtcttac    6780
cgggttggac tcaagacgat agttaccgga taaggcgcag cggtcgggct gaacggggggg    6840 ttcgtgcaca cagcccagct tggagcgaac gacctacacc gaactgagat acctacagcg    6900
tgagctatga gaaagcgcca cgcttcccga agggagaaag gcggacaggt atccggtaag    6960
cggcagggtc ggaacaggag agcgcacgag ggagcttcca gggggaaacg cctggtatct    7020
ttatagtcct gtcgggtttc gccacctctg acttgagcgt cgatttttgt gatgctcgtc    7080 agggggggcgg agcctatgga aaacgccag caacgcggcc ttttacggt tcctggcctt    7140 ttgctggcct tttgctcaca tggctcgac                                     7169
```

<210> SEQ ID NO 6
<211> LENGTH: 223
<212> TYPE: PRT
<213> ORGANISM: Homo sapiens

<400> SEQUENCE: 6

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro

```
            20                  25                  30
Val Phe Cys Lys Ala Met His Val Ala Gln Pro Ala Val Leu Ala
         35                  40                  45

Ser Ser Arg Gly Ile Ala Ser Phe Val Cys Glu Tyr Ala Ser Pro Gly
 50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
                115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
210                 215                 220

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gctggttgtt gtgctgtctc                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gaggtgccag tgcatgtaga                                          20

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
cgctgtgggc tcttctctta cat                                      23

<210> SEQ ID NO 10
<211> LENGTH: 22
<212> TYPE: DNA
<213> ORGANISM: Artificial Sequence
```

```
<220> FEATURE:
<223> OTHER INFORMATION: Synthetic primer

<400> SEQUENCE: 10
gagcaagcca tggctaagct ta                                              22

<210> SEQ ID NO 11
<211> LENGTH: 7
<212> TYPE: PRT
<213> ORGANISM: Sus sp.

<400> SEQUENCE: 11

Gly Gly Ser Gly Gly Ala Ala
1               5
```

TRANSGENIC UNGULATES EXPRESSING CTLA4-IG AND USES THEREOF

This application is a continuation of U.S. patent application Ser. No. 11/990,246, filed February 2009, which is a national stage entry of PCT/US06/30842, filed Aug. 9, 2006, which claims priority U.S. Provisional Patent Application No. 60/706,843, filed Aug. 9, 2005.

FIELD OF THE INVENTION

The present invention provides transgenic ungulates, such as pigs, expressing cytoxic T-lymphocyte associated protein 4 (CTLA4) fused to an immunoglobulin (Ig) (CTLA4-Ig), as well as organs, tissues, cells and cell lines derived therefrom. The invention also provides transgenic ungulates, and organs, tissues, cells and cell lines derived therefrom, expressing CTLA4 under the control over a tissue-specific promoter. These ungulates, including organs, tissues, cells and cell lines derived therefrom, can be used in research and medical therapy, including xenotransplantation. In addition, methods are provided to prepare organs, tissues, and cells expressing CTLA4-Ig for use in xenotransplantation, as well as nucleic acid constructs and vectors useful therein.

BACKGROUND

The success of allogeneic (human to human) organ transplantation has been established in the last few decades, due to the limited supply of donor organs, many patients have little or no chance of receiving a transplanted organ, such as a kidney, heart or liver. A significant number of people die while awaiting an organ. Ungulate animals, such as porcine, ovine and bovine, are considered likely sources of xenograft organs and tissues. Porcine xenografts have been given the most attention since the supply of pigs is plentiful, breeding programs are well established, and their size and physiology are compatible with humans. However, there are several obstacles that must be overcome before the transfer of these organs or tissues into humans can be successful.

The immunological barriers to xenografts differ from those to allografts because of the greater molecular incompatibility between host and donor tissue. This results in a much greater role of the innate immune system, including naturally occurring antibodies, complement, and immune cells, in the rejection process than occurs in allotransplantation. This fundamental difference raises the height of the barrier considerably and is a major reason xenotransplantation is not a current clinical reality.

The first immunological hurdle is "hyperacute rejection" (HAR). HAR is defined by the ubiquitous presence of high titers of pre-formed natural antibodies binding to the foreign tissue. The binding of these natural antibodies to target epitopes on the donor tissue endothelium is believed to be the initiating event in HAR. This binding, within minutes of perfusion of the donor tissue with the recipient blood, is followed by complement activation, platelet and fibrin deposition, and ultimately by interstitial edema and hemorrhage in the donor organ, all of which cause rejection of the tissue in the recipient (Strahan et al. (1996) Frontiers in Bioscience 1, e34-41). The primary course of HAR in humans is the natural anti-galactose alpha 1,3-galactose antibody, which comprises approximately 1% of antibodies in humans and monkeys. Except for Old World monkeys, apes and humans, most mammals carry glycoproteins on their cell surfaces that contain the galactose alpha 1,3-galactose epitope (Galili et al., J. Biol. Chem. 263: 17755-17762, 1988). In contrast, glycoproteins that contain galactose alpha 1,3-galactose are found in large amounts on cells of other mammals, such as pigs. Humans, apes and old world monkeys do not express galactose alpha 1,3-galactose, but rather produce in high quantities a naturally occurring anti-galactose alpha 1,3-galactose antibody (Cooper et al., Lancet 342:682-683, 1993). It binds specifically to glycoproteins and glycolipids bearing galactose alpha-1,3 galactose. Alpha 1,3 galactosyltransferase is the enzyme that forms the galactose alpha-1,3 galactose epitopes on cells.

A recent, major breakthrough in the field of xenotransplantation was the production of the first live pigs lacking any functional expression of alpha 1,3 galactosyltransferase (Phelps et al. Science 299:411-414 (2003))

PCT publication No. WO 04/028243 by Revivicor, Inc. describes the successful production of viable pigs, as well as organs, cells and tissues derived therefrom, lacking any functional expression of alpha 1,3 galactosyltransferase. PCT Publication No. WO 04/016742 by Immerge Biotherapeutics, Inc. also describes the production of alpha 1,3 galactosyltransferase knock-out pigs.

The next significant barrier to xenotransplantation is delayed xenograft rejection, otherwise known as acute vascular rejection. This form of rejection invariably occurs in discordant vascularised xenografts in which HAR is prevented. The pathogenesis of delayed xenograft rejection, though poorly understood, is characterized by a distinct and often intractable inflammatory process, which can occur within 36-48 hours but typically occurs days to months after transplantation. Delayed xenograft rejection is characterized by the infiltration of recipient inflammatory cells and thrombosis of graft vessels, leading to ischaemia. Various strategies are currently under investigation to prevent delayed xenograft rejection, for example, PCT Publication No. WO 98/42850 by Imperial College discloses that the expression of coagulation inhibitors on the surface of the xenograft can inhibit the thrombotic aspect of this type of rejection.

The final major barrier encountered by xenografts is cell mediated rejection. The differences between recipients and allograft donor organs are largely restricted to small differences in the MHC antigens. There is predominantly direct recognition of these differences by host T cells and a predominantly Th1 type response occurs.

T-cell activation is involved in the pathogenesis of transplant rejection. Activation of T-cells requires at least two sets of signaling events. The first is initiated by the specific recognition through the T-cell receptor of an antigenic peptide combined with major histocampatibility complex (MHC) molecules on antigen presenting cells (APCs). The second set of signals is antigen nonspecific and is delivered by T-cell costimulatory receptors interacting with their ligands on APCs. In the absence of costimulation, T-cell activation is impaired or aborted, which may result in an antigen specific unresponsive state of clonal anergy, or in deletion by apoptotic death. Hence, the blockade of T-cell costimulation has been thought to provide an approach for suppressing unwanted immune responses in an antigen specific manner while preserving normal immune functions. (Dumont, F. J. 2004 Therapy 1, 289-304).

Of several T cell costimulatory pathways identified to date, the most prominent is the CD28 pathway. CD28, a cell surface molecule expressed on T-cells, and its counter receptors, the B7.1 (CD80) and B7.2 (CD86) molecules, present on dendritic cells, macrophages, and B-cells, have been characterized and identified as attractive targets for interrupting T-cell costimulatory signals. A second T-cell surface molecule homologous to CD28 is known as cytoxic T-lymphocyte associated protein 4 (CTLA4). CTLA4 is a cell surface signaling molecule, but contrary to the actions of CD28, CTLA4 negatively regulates T cell function. CTLA4 has 20-fold higher affinity for the B7 ligands than CD28. The gene for human CTLA4 was cloned in 1988 and chromosomally mapped in 1990 (Dariavach et al., Eur. J. Immunol. 18:1901-1905 (1988); Lafage-Pochitaloff et al., Immunogenetics 31:198-201 (1990); U.S. Pat. No. 5,977,318).

The CD28/B7 pathway has become an attractive target for interrupting T cell costimulatory signals. The design of a CD28/B7 inhibitor has exploited the endogenous negative regulator of this system, CTLA4. A CTLA4-immunoglobulin (CTLA4-Ig) fusion protein has been studied extensively as a means to inhibit T cell costimulation. A difficult balance must be reached with any immunosuppressive therapy; one must provide enough suppression to overcome the disease or rejection, but excessive immunosuppression will inhibit the entire immune system. The immunosuppressive activity of CTLA4-Ig has been demonstrated in preclinical studies of animal models of organ transplantation and autoimmune disease.

Soluble CTLA4 has recently been tested in human patients with kidney failure, psoriasis and rheumatoid arthritis. Bristol-Myers Squibb's drug Abatacept, soluble CTLA4-Ig has recently been approved for the treatment of rheumatoid arthritis. This drug is the first in the new class of selective T cell costimulation modulators. Bristol-Myers Squibb is also conducting Phase II clinical trials with Belatacept (LEA29Y) for allograft kidney transplants. LEA29Y is a mutated form of CTLA4, which has been engineered to have a higher affinity for the B7 receptors than wild-type CTLA4, fused to immunoglobulin. Repligen Corporation is also conducting clinical trials with its CTLA4-Ig for idiopathic thrombocytopenic purpura.

Although CTLA-4 from one organism is able to bind to B7 from another organism, the highest avidity is found for allogeneic B7. Thus, while soluble CTLA-4 from the donor organism can thus bind to both recipient B7 (on normal cells) and donor B7 (on xenotransplanted cells), it preferentially binds B7 on the xenograft. Thus, for applications in xenotransplantation, particularly pig to human, porcine CTLA4 could be used to induce immunosuppression. PCT Publication No. WO 99/57266 by Imperial College discloses the porcine CTLA4 sequence and the administration of soluble CTLA4-Ig for xenotransplantation therapy. Vaughn A. et al., Journal of Immunology (2000) 3175-3181, describes binding and function assays demonstrating species specificity in the action of soluble porcine CTLA4-Ig.

To date, much of the research on CTLA4-Ig as an immunosuppressive agent has focused on administering soluble forms of CTLA4-Ig to a patient. Transgenic mice engineered to express CTLA4-Ig have been created and subject to several lines of experimentation. Ronchese et al. examined immune system function generally after expression of CTLA4 in mice (Ronchese et al. J Exp Med (1994) 179: 809; Lane et al. J Exp Med. 1994 Mar. 1; 179(3):819). Sutherland et al. (Transplantation. 2000 69(9):1806-12) described the protective effect of CTLA4-Ig secreted by transgenic fetal pancreas allografts in mice to test the effects of transgenically expressed CTLA4-Ig on allogenic islet transplantation. Lui et al. (J Immunol Methods 2003 277: 171-183) reported the production of transgenic mice that expressed CTLA4-Ig under control of a mammary specific promoter to induce expression of soluble CTLA4-Ig in the milk of transgenic animals for use as a bioreactor.

PCT Publication No. WO 01/30966 by Alexion Pharmaceuticals, Inc. describes chimeric DNA constructs containing the T cell inhibitor CTLA-4 attached to the complement protein CD59, as well as transgenic porcine cells, tissues, and organs containing the same.

Martin C. et al., Transgenic Research (2005) 14: 373-384, describes transgenic fetal porcine neurons that express human CTLA4-Ig under the control of the neuron-specific enolase promoter for use in the cellular transplantation of neurons to treat human neurodegenerative disorders.

It is object of the present invention to provide ungulate organs, cells and tissues which decrease the immune response of humans on transplantation.

It is another object of the present invention to provide methods to decrease the immune response of humans on transplantation of ungulate organs, cells and tissues.

SUMMARY OF THE INVENTION

The present invention provides transgenic ungulates, organs, tissues and cells for xenotransplantation that have been genetically modified to reduce or avoid cell mediated rejection encountered by the recipient's immune system. The ungulate may be, for example, porcine, bovine, ovine or equine. In particular, the present invention provides transgenic pigs, and organs, tissues and cells derived therefrom, for xenotransplantation.

In one aspect, the present invention is a transgenic ungulate that expresses a CTLA4 peptide, or a biologically active fragment or derivative thereof, wherein the CTLA4 peptide is fused to an immunoglobulin (Ig), or a biologically active fragment or derivative thereof. In one embodiment, the CTLA4 peptide is porcine CTLA4. In another embodiment, the CTLA4 peptide is human CTLA4.

In one embodiment, the CTLA4 peptide is full length CLTA4. In another embodiment, the CTLA4 peptide is truncated. In a particular embodiment, at least the transmembrane domain of CTLA4 has been removed. In another particular embodiment, the CTLA peptide is the extracellular domain of CTLA4. In a further embodiment, the CTLA4 peptide is mutated. A non-limiting example of a mutated CTLA4 peptide is a human CTLA4 peptide mutated by substitution of (i) an alanine at position +29 with a tryptophan, and (ii) a leucine at position +104 with a glutamic acid. In another embodiment, the CTLA4 peptide is modified. The modification may be, for example, addition of an intracellular retention signal.

In one embodiment, the immunoglobulin is human Ig. In another embodiment, the immunoglobulin is porcine Ig. In a particular embodiment, the human or porcine Ig is IgG. In a specific embodiment, the immunoglobulin is IgG1 or IgG4.

In one embodiment, the CTLA4 peptide is porcine and the Ig is human. In another embodiment, the CTLA4 peptide is human and the Ig is porcine.

The present invention further includes tissues, organs and cells derived from a transgenic ungulate that expresses a CTLA4 peptide, or a biologically active fragment or derivative thereof, wherein the CTLA4 peptide is fused to an immunoglobulin (Ig), or a biologically active fragment or derivative thereof.

In a second aspect, the present invention is a non-human transgenic cell comprising a nucleotide sequence encoding human CTLA4 and a nucleotide sequence encoding porcine CTLA4. The present invention also includes tissues, organs or animals including the non-human transgenic cell encoding human CTLA4 and a nucleotide sequence encoding porcine CTLA4.

In a third aspect, the present invention is a transgenic ungulate, such as a pig, that expresses a CTLA4 peptide, wherein expression of the CTLA4 peptide is under the control of a tissue-specific promoter, a tissue-specific enhancer or both. In one embodiment, the expression of the CTLA4 peptide is under the control of a tissue-specific promoter. Tissue-specific promoters include, but are not limited to, liver-specific promoters, lymphoid-specific promoters, T-cell receptor and immunoglobulin promoters, endothelial promoters, pancreas-specific promoters, and mammary gland-specific promoters.

In a fourth aspect, the present invention is a transgenic animal, such as a pig, that expresses a CTLA4 peptide, wherein expression of the CTLA4 peptide is under the control of a regulatable promoter. Regulatable promoters include, but are not limited to, metallothionein promoters, tetracycline-regulated promoters, ecdysone-inducible promoter, cytochrome P450 inducible promoters, CYP1A1 promoters, and mifepristone promoters. The animal may be, for example, an ungulate. In a particular embodiment, the animal is a pig.

According to a fifth aspect of the invention, the transgenic cells, tissues, organs or animals of the present invention are further characterized by one or more additional genetic modifications (i.e., in addition to transgenic expression of CTLA4 or CTLA4-Ig). In one embodiment, the additional genetic modification eliminates or reduces functional expression of a gene. The gene may be, for example, the alpha-1, 3-galactosyltransferase ($\alpha(1,3)$GT) gene. In another embodiment, the additional genetic modification imparts functional expression of a gene, such as tissue factor pathway inhibitor (TFPI) or a complement inhibitor gene (e.g., decay accelerating factor (DAF)). In a particular embodiment, the cells, tissues, organs or animals of the present invention are characterized by two or more additional genetic modifications.

In a sixth aspect, the present invention is a method of reducing or eliminating cell mediated rejection of a xenotransplant in a recipient comprising providing xenogenic cells, tissues or organs to a recipient which have been genetically modified to express CTLA4 fused to an immunoglobulin (Ig). In one embodiment, the CTLA4 peptide is porcine. In another embodiment, the CTLA4 peptide is human. In a still further embodiment, the cells, tissue or organs have been genetically modified to express human CTLA4 and porcine CTLA4.

In one embodiment, the method also includes administering soluble CTLA4 to the recipient. In a particular embodiment, the soluble CTLA4 is porcine. In another particular embodiment, the soluble CTLA4 is human.

In a seventh aspect, the present invention is a method of reducing or eliminating cell mediated rejection of a xenotransplant in a recipient comprising providing xenogenic cells, tissues or organs to a recipient which have been genetically modified to express a CTLA4 peptide, wherein the expression of CTLA4 peptide is under the control of a tissue-specific promoter, tissue-specific enhancer or both. In one embodiment, the expression of CTLA4 peptide is under the control of a tissue-specific promoter. In one embodiment, the CTLA4 peptide is porcine. In another embodiment, the CTLA4 peptide is human. The tissue specific promoter may be, for example, a liver-specific promoter, a lymphoid-specific promoter, a T-cell receptor and immunoglobulin promoter, an endothelial promoter, a pancreas-specific promoter or a mammary gland-specific promoters.

In one embodiment of the method, the cells, tissues or organs are characterized by one or more additional genetic modifications. In another embodiment, the cells, tissue or organs have been genetically modified to express human CTLA4 and porcine CTLA4.

Optionally, the method also includes administering soluble CTLA4 to the recipient which may be, for example, human or porcine soluble CTLA4.

An eighth aspect of present invention is a method for producing a transgenic ungulate that expresses a CTLA4 peptide fused to an immunoglobulin (Ig), which method involves introducing a nucleic acid construct or vector encoding the CTLA4 peptide fused to an immunoglobulin molecule into the genome of an ungulate cell. Any suitable method can be used to introduce the construct or vector into the genome, including, for example, transfection. Representative, non-limiting, methods of transfection suitable for use in the present invention include electroporation and lipofection. In one embodiment, the construct or vector integrates into the genome. Integration may be random or targeted. Optionally, the expression of the CTLA4 peptide is under the control of a tissue-specific promoter (or enhancer or combination of promoter and enhancer) or regulatable promoter.

An ninth aspect of the present invention is a nucleic acid construct which includes a nucleotide sequence encoding a CTLA4 peptide operably linked to a tissue specific promoter, wherein the promoter is not a mammary-specific promoter. The tissue specific promoter may be, for example, a liver-specific promoter, a lymphoid-specific promoter, a T-cell receptor and immunoglobulin promoter, an endothelial promoter, a pancreas-specific promoter. In a particular embodiment, the tissue specific promoter is a pancreas-specific promoter. In another embodiment, the promoter is not a neuron-specific promoter.

BRIEF DESCRIPTION OF THE FIGURES

FIG. 1 depicts the amino acid sequence of porcine CTL4 (SEQ ID NO:1). Residues approximately −30 to 0 represent the signal sequence; residues approximately 1-122 represent the extracellular domain; residues approximately 123-149 represent the transmembrane domain and residues approximately 150 to 183 represent the cytoplasmic domain.

FIG. 2 depicts the nucleic acid sequence of porcine CTLA4 (SEQ ID NO:2).

FIG. 3 depicts the amino acid sequence of a porcine CTLA4 construct (SEQ ID NO:3). The underlined sequence shows the flexible linker GGSGGAA, which denotes the junction between CTLA4 and Ig.

FIG. 5 depicts the complete vector DNA sequence for the construct pREV 785 (SEQ ID NO:4).

FIG. 7 depicts the complete vector DNA sequence for the construct pREV 792 (SEQ ID NO:5).

DETAILED DESCRIPTION

Figure 4:
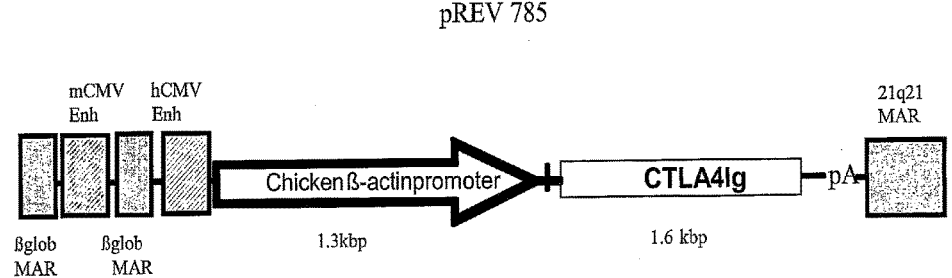
FIG. 4 depicts a schematic diagram of the pREV785 construct as described in Example 1.

The present invention provides transgenic non-human animal organs, tissues and cells for xenotransplantation that have been genetically modified to reduce or avoid the cell mediated rejection encountered by the recipient's immune system. In particular, the invention provides transgenic ungulates, such as pigs, that have been have been genetically modified to express a cytoxic T-lymphocyte associated protein 4 (CTLA4) peptide or CTLA4 fused to an immunoglobulin (Ig) (CTLA4-Ig). Optionally, the expression of the CTLA4 peptide is under the control of a regulatable promoter or a tissue-specific promoter, enhancer or combination thereof.

In certain embodiments, it is believed that the species specificity exhibited by CTLA4 may provide a level of immunosuppression that reduces the cell mediated rejection of the xenograft, but not suppression of the recipients normal immune function. For example, species specificity of porcine CTLA4 may provide a level of immunosupression that reduces rejection of a porcine xenograft in a human recipient, but does not reduce suppression of the recipient's immune system.

In one aspect of the present invention, transgenic animals such as pigs are provided that express a CTLA4 peptide or a biologically active fragment or derivative thereof. In another embodiment, transgenic animals are provided that express a CTLA4-Ig fusion peptide. The transgenic animals of the present invention are useful as a source of organs, tissues, cells or cell lines for research or therapeutic use, such as xenotransplanation.

In one embodiment, the CTLA4 peptide can be a porcine CTLA4 peptide, or a biologically active fragment or derivate thereof. In another embodiment, the CTLA4 peptide can be a human CTLA4 peptide, or a biologically active fragment or derivative thereof. In one embodiment, the CTLA4 can be a truncated form of CTLA4, for example, in which at least the transmembrane domain of the protein has been removed. Optionally, the CLT4 peptide is the extracellular domain of CTLA4. The CTLA4 peptide can also be mutated, for example, by one or more amino acid substitutions.

In another embodiment, the CTLA4 peptide can be modified such that it is expressed intracellularly. For example, the CTLA4 peptide can be modified to include an intracellular retention signal such as a golgi retention signal.

In further embodiments, the CTLA4 peptide can be fused to a peptide dimerization domain.

In one embodiment, the CTLA4 peptide can be fused to an immunoglobulin (Ig). In another embodiment, the CTLA4 fusion peptides can include a linker sequence that can join the two peptides.

In further embodiments of the present invention, both human and porcine CTLA4 can be expressed transgenically in the animal.

In one embodiment, the invention provides a transgenic ungulate that expresses a CTLA4 peptide, or a biologically active fragment or derivative thereof, wherein the CTLA4 peptide is fused to an immunoglobulin (Ig), or a biologically active fragment or derivative thereof. In a particular embodiment, the immunoglobulin is human. In another particular embodiment, the immunoglobulin is porcine. The CTLA4 peptide and the immunoglobulin need not be from the same species. For example the CTLA4 peptide can be porcine and the Ig human. CTLA4 may be fused to a fragment, portion or region of the immunoglobulin, such as a constant region.

In another embodiment, methods to reduce and/or eliminate cell mediated rejection of xenotransplants are provided in which human CTLA4 can be expressed transgenically in an animal such as a pig, the organs and/or tissues can be transplanted into a recipient and soluble porcine CTLA4 can be administered to the recipient.

In an alternate embodiment, porcine CTLA4 can be expressed transgenically in an animal such as a pig, the organs and/or tissues can be transplanted into a recipient and soluble human CTLA4 can be administered to the recipient.

The CTLA4 transgenic animals can be used as a source of tissue and/or organs for transplantation therapy. A pig embryo prepared in this manner or a cell line developed therefrom can also be used in cell-transplantation therapy.

The present invention is also directed to a non-human transgenic cell comprising a nucleotide sequence encoding human CTLA4 and a nucleotide sequence encoding porcine CTLA4, as well as tissues, organs and animals that include such cells.

The animals, tissue, organs, cells and cell lines of the present invention transgenically express CTLA4 or CTLA4-Ig, but can be further characterized by additional genetic modifications. These include, for example, genetic modifications that can reduce or eliminate expression of a particular gene, or provide expression of a particular gene. For example, the animals, organs tissues or cells of the present invention may transgenically express CTLA4 and lack any functional expression of alpha 1,3 galactosyltranferase. As a further example, the animals, organs tissue or cells of the present invention may transgenically express CTLA4 and further transgenically express tissue factor pathway inhibitor (TFPI) or a complement inhibitor gene (e.g., decay accelerating factor (DAF), MCP (CD46), or CD59).

In another aspect of the present invention, nucleic acid constructs and vectors are provided to allow the expression of CTLA4 in transgenic animals. In one embodiment, the nucleic acid construct contains a regulatory sequence operably linked to the CTLA4 sequence. In one embodiment, the regulatory sequence can be a promoter sequence. In one embodiment, the promoter can be a regulateable promoter. In another embodiment, the promoter can be a tissue specific promoter. In a further embodiment, the promoter can be a ubiquitous promoter. In still further embodiments, the nucleic acid construct or vector can contain a selectable marker gene to identify cells that express the CTLA4 peptide. The nucleic acid construct can optionally include a gene enhancer. Tissue specificity can be imparted by the tissue-specific promoter, a tissue specific gene enhancer or a combination of both a tissue specific promoter and a tissue specific enhancer.

In another aspect of the present invention, methods are provided to produce transgenic animals expressing CTLA4 or CTLA-Ig. In one embodiment, electroporation or lipofection of the constructs encoding the CTLA4 or CTLA4-Ig can be used to produce the transgenic animals.

In a further aspect of the present invention, an ungulate such as a pig can be prepared by a method in accordance with any aspect of the present invention. Genetically modified pigs that express CTLA4 can be used as a source of tissue and/or organs for transplantation therapy. Pig embryos prepared in this manner or a cell line developed therefrom can be used in cell-transplanation therapy.

Organs and tissues derived from the transgenic pigs of the present invention can be used in xenotransplatation. In one embodiment, after transplantation of the improved organs and tissues of the present invention, the organs and tissues can function in a primate, including, but not limited to humans and monkeys, for at least approximately 120, 150, 200, 300, 365 days in the recipient.

Definitions

A "target DNA sequence" is a DNA sequence to be modified by homologous recombination. The target DNA can be in any organelle of the animal cell including the nucleus and mitochondria and can be an intact gene, an exon or intron, a regulatory sequence or any region between genes.

A "targeting DNA sequence" is a DNA sequence containing the desired sequence modifications and which is, except for the sequence modifications, substantially isogenic with the target DNA.

A "homologous DNA sequence or homologous DNA" is a DNA sequence that is at least about 85%, 90%, 95%, 98% or 99% identical with a reference DNA sequence. A homologous sequence hybridizes under stringent conditions to the target sequence, stringent hybridization conditions include those that will allow hybridization occur if there is at least 85% and preferably at least 95% or 98% identity between the sequences.

An "isogenic or substantially isogenic DNA sequence" is a DNA sequence that is identical to or nearly identical to a reference DNA sequence. The term "substantially isogenic" refers to DNA that is at least about 97-99% identical with the reference DNA sequence, and preferably at least about 99.5-99.9% identical with the reference DNA sequence, and in certain uses 100% identical with the reference DNA sequence.

"Homologous recombination" refers to the process of DNA recombination based on sequence homology.

"Gene targeting" refers to homologous recombination between two DNA sequences, one of which is located on a chromosome and the other of which is not.

"Non-homologous or random integration" refers to any process by which DNA is integrated into the genome that does not involve homologous recombination.

A "selectable marker gene" is a gene, the expression of which allows cells containing the gene to be identified. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype can be, for example, the production of luminescence or the production of a colored compound, or the production of a detectable change in the medium surrounding the cell.

The term "porcine" refers to any pig species, including pig species such as, for example, Large White, Landrace, Meishan, and Minipig.

The term "ungulate" refers to any hoofed mammal Non-limiting examples of ungulates include ovine, bovine, porcine and equine.

The term "ovine" refers to any sheep species, including sheep species such as, for example, *Ovis aries*.

The term "bovine" refers to any cattle species, including cattle species such as, for example, *Bos primigenius taurus*. Cattle are commonly referred to as cows.

The term "equine" refers to any horse species.

The term "oocyte" describes the mature animal ovum which is the final product of oogenesis and also the precursor forms being the oogonium, the primary oocyte and the secondary oocyte respectively.

DNA (deoxyribonucleic acid) sequences provided herein are represented by the bases adenine (A), thymine (T), cytosine (C), and guanine (G).

Amino acid sequences provided herein are represented by the following abbreviations:

| | |
|---|---|
| A | alanine |
| P | proline |
| B | aspartate or asparagine |
| Q | glutamine |
| C | cysteine |
| R | arginine |
| D | aspartate |
| S | serine |
| E | glutamate |
| T | threonine |
| F | phenylalanine |
| G | glycine |
| V | valine |
| H | histidine |
| W | tryptophan |
| I | isoleucine |
| Y | tyrosine |
| Z | glutamate or glutamine |
| K | lysine |
| L | leucine |
| M | methionine |
| N | asparagine |

"Transfection" refers to the introduction of DNA into a host cell. Most cells do not naturally take up DNA. Thus, a variety of technical "tricks" are utilized to facilitate gene transfer. Numerous methods of transfection are known to the ordinarily skilled artisan, for example, $CaPO_4$ and electroporation. (J. Sambrook, E. Fritsch, T. Maniatis, Molecular Cloning: A Laboratory Manual, Cold Spring Laboratory Press, 1989). Transformation of the host cell is the indicia of successful transfection.

The term "regulatable" promoter as used herein refers to genomic sequences that are capable of either inducing or suppressing the expression of a gene in response to a stimulus. Non-limiting examples of regulatable promoters include: metallothionein promoters, tetracycline-regulated promoters, ecdysone-inducible promoter, cytochrome P450 inducible promoters, CYP1A1 promoters, and mifepristone promoters.

I. CTLA4 Peptides

The present invention provides transgenic animals organs and tissues, such as ungulate organs or tissues, for xenotransplantation that have been genetically modified to reduce or avoid the cell mediated rejection encountered by the recipient's immune system. In particular, the present invention provides genetically modified pig organs and tissues for xenotransplant.

In one aspect of the present invention, transgenic animals are provided that express CTLA4 peptide or a biologically active fragment or derivative thereof. In particular, the invention provides transgenic porcine animals that have been genetically modified to express a cytoxic T-lymphocyte associated protein 4-immunoglobin (CTLA4-Ig) protein. In one embodiment, the CTLA4 peptide can be a porcine CTLA4 peptide. In another embodiment, the CTLA4 peptide can be a human CTLA4 peptide. In a particular embodiment, the CTLA4 peptide includes only the extracellular domain of the peptide.

CTLA4 peptides contain four domains: a signal sequence, an extracellular domain, a transmembrane domain and a cytoplasmic domain. For example, for the human CTLA4 peptide shown below (SEQ ID NO:6), the signal peptide is represented by approximately the first 30-35 amino acids (lowercase letters, underlined), the extracellular domain is represented by approximately the next 116 amino acids (capital letters, bold); the transmembrane region is represented by approximately the following 37 amino acids (lowercase letters) and the cytoplasmic domain is represented by approximately the last 33 amino acids (capital letters).

Human CTLA4

(SEQ ID NO: 6)

maclgfqrhkaqlnlatrtwpctllffllfipvfckaMHVAQPAVVLASSRGIASFVCEYASPGKA

TEVRVTVLRQADSQVTEVCAATYMMGNELTFLDDSICTGTSSGNQVNLTI

QGLRAMDTGLYICKVELMYPPPYYLGIGNGTQIYVIDpepcpdsdfllwilaavssglf fysflltavslskmlKKRSPLTTGVYVKMPPTEPECEKQFQPYFIPIN

FIG. 1 depicts the amino acid sequence for porcine CTLA4. Residues approximately −30 to 0 represent the signal sequence; residues approximately 1-122 represent the extracellular domain, residues approximately 123-149 represent the transmembrane domain and residues approximately 150 to 183 represent the cytoplasmic domain.

In one embodiment, the CTL4 peptide is the full length CTLA4. In a further embodiment, the CTLA4 peptide can contain less than the full length CTLA4 protein. In one embodiment, the CTLA4 peptide can contain the extracellular domain of a CTLA-4 peptide. In a particular embodiment, the CTLA4 peptide is the extracellular domain of CTLA4. In still further embodiments, the present invention provides mutated forms of CTLA4. In one embodiment, the mutated form of CTLA4 can have higher affinity than wild type for porcine and/or human B7. In one specific embodiment, the mutated CTLA4 can be human CTLA4 (Glu104, Tyr29).

In one embodiment, the CTLA4 can be a truncated form of CTLA4, in which at least the transmembrane domain of the protein has been removed. In another embodiment, the CTLA4 peptide can be modified such that it is expressed intracellularly. In one embodiment, a golgi retention signal can be added to the N or C terminus of the CTLA4 peptide. In one embodiment, the golgi retention signal can be the sequence KDEL, which can be added to the C or N terminal of the CTLA4 peptide. In further embodiments, the CTLA4 peptide can be fused to a peptide dimerization domain. In one embodiment, the CTLA4 peptide can be fused to an immunoglobulin (Ig). In another embodiment, the CTLA4 fusion peptides can include a linker sequence that can join the two peptides.

Any human CTLA4 sequences or biologically active portion or fragment thereof known to one skilled in the art can be according to the compositions and methods of the present invention. Non-limiting examples include, but are not limited to the following Genbank accession numbers that describe human CTLA4 sequences: NM005214.2; BC074893.2; BC074842.2; AF414120.1; AF414120; AY402333; AY209009.1; BC070162.1; BC069566.1; L15006.1; AF486806.1; AC010138.6; AJ535718.1; AF225900.1; AF225900; AF411058.1; M37243.1; U90273.1; and/or AF316875.1. Further nucleotide sequences encoding CTLA4 peptides can be selected from those including, but not limited to the following Genbank accession numbers from the EST database: CD639535.1; AI733018.1; BM997840.1; BG536887.1; BG236211.1; BG058720.1; AI860199.1; AW207094.1; AA210929.1; AI791416.1; BX113243.1; AW515943.1; BE837454.1; AA210902.1; BF329809.1; AI819438.1; BE837501.1; BE837537.1; and/or AA873138.1.

Porcine CTLA4 was cloned by Lechler et al. in 1988, see, for example, WO 99/57266 to Imperial College. In one embodiment, the porcine CTLA4 peptide or fragments thereof, as well as nucleic acids encoding the same, which can be used according to the present invention is disclosed in FIG. 1 (SEQ ID NO:1). In a particular embodiment, the extracellular domain of porcine CTLA4 can be used according to the present invention, for example, amino acid residues 1-122 as depicted in FIG. 1, as well as nucleic acids encoding the same. In another embodiment, the porcine CTLA4 nucleic acid sequence or fragments thereof that can be used according to the present invention is disclosed in FIG. 2.

In additional embodiments, any consensus CTLA4 peptide can be used according to the present invention. In another embodiment, nucleic acid and/or peptide sequences at least 80%, 85%, 90% or 95% homologous to the CTLA4 peptides and nucleotide sequences described herein. In further embodiments, any fragment or homologous sequence that exhibits similar activity as CTLA4 can be used.

In other embodiments, the amino acid sequence which exhibits T cell inhibitory activity can be amino acids 38 to 162 of the porcine CTLA4 sequence or amino acids 38 to 161 of the human CTLA4 sequence (see, for example, PCT Publication No. WO 01/30966). In one embodiment, the portion used should have at least about 25% and preferably at least about 50% of the activity of the parent molecule.

CTLA4-Immunoglobulin Fusion Peptides

In other embodiments, the CTLA4 nucleic acids and peptides of the present invention can be fused to immunoglobulin genes and molecules or fragments or regions thereof. Reference to the CTLA4 sequences of the present invention include those sequences fused to immunoglobulins.

In one embodiment, the Ig can be a human Ig. In another embodiment, the Ig can be IgG, in particular, IgG1. In another embodiment, the Ig can be the constant region of IgG. In a particular embodiment, the constant region can be the Cγ1 chain of IgG1. In one particular embodiment of the present invention, the extracellular domain of porcine CTLA4 can be fused to human Cγ1 Ig. In another particular embodiment, the extracellular domain of human CTLA4 can be fused to IgG1 or IgG4. In a further particular embodiment, the extracellular domain of mutated CTLA4 (Glu 104, Tyr 29) can be fused to IgG1. In a specific embodiment, the CTLA-Ig fusion peptide can be that illustrated in FIG. 3 (SEQ ID NO:3).

In another embodiment of the present invention, linker sequences can be used to join the nucleic acid sequences encoding the CTLA4 peptide with the nucleic acid sequences encoding the Ig. In one non-limiting embodiment, the linker sequence can be a flexible linker, for example, the sequence GGSGGAA (SEQ ID NO:11).

In further embodiments of the present invention, both human and porcine CTLA4 can be expressed transgenically in the porcine animal. In another embodiment, methods to reduce and/or eliminate cell mediated rejection are provided in which human CTLA4 can be expressed transgenically in a pig, the organs and/or tissues can be transplanted into a recipient and soluble porcine CTLA4 can be administered to the recipient. In an alternate embodiment, porcine CTLA4 can be expressed transgenically in a pig, the organs and/or tissues can be transplanted into a recipient and soluble human CTLA4 can be administered to the recipient.

In other embodiments of the present invention, any human immunoglobulin can be fused to the CTLA4 peptides described herein. In particular, the following human immunoglobins can be used: IgG1, IgG2, IgG3, IgM, IgE, IgA, and IgD, or fragments thereof that retain biological activity. In particular, the constant region of these immunoglobulins can be fused to a CTLA4 peptide of the present invention. Such human immunoglobulins are commonly known to one skilled in the art. For example, one skilled in the art can search the Genbank database using the query term "IgH@" and/or Ig@.

In other embodiments, nucleic acid encoding a peptide containing an immunoglobulin region, such as the constant region, can be obtained from human immunoglobulin mRNA present in B lymphocytes. In another embodiment, nucleic acids encoding an immunoglobulin region, such as the constant region, can be obtained from B cell genomic DNA. For example, DNA encoding Cγ1 or Cγ4 can be cloned from either a cDNA or a genomic library or by polymerase chain reaction (PCR) amplification in accordance with protocols known to one skilled in the art. The nucleic acids of the invention can be DNA or RNA. In a particular embodiment, the nucleic acid encoding an immunoglobulin constant region can contain all or a portion of the following non-limiting examples: the DNA encoding human Cγ1 (Takahashi, N. S. et al. (1982) Cell 2:671-679), the DNA encoding human Cγ2 (Kabat, E. A, T. T. Wu, M. Reid-Miller, H. M. Perry, and K. S. Gottesman eds. (1987) "Sequences of Proteins of Immunological Interest" National Institutes of Health, Bethesda, Md.); the DNA encoding human Cγ3 (Huck, S., et al. (1986) Nucl. Acid Res. 14:1779); and the DNA encoding human Cγ4 (Kabat et al., (1987) "Sequences of Proteins of Immunological Interest" National Institutes of Health, Bethesda, Md.).

II. Expression of CTLA4 Peptides

In another aspect of the present invention, nucleic acid constructs and vectors are provided to allow the expression of CTLA4 in animals such as ungulates. In one embodiment, the nucleic acid construct contains a nucleotide sequence that encodes all or part of a CTLA4 peptide, such as those CTLA4 peptides described above. In another embodiment, the nucleic acid construct contains a nucleotide sequence that encodes all or part of a CTLA4 peptide (such as those described above) fused to a nucleotide sequence encoding all or part of an immunoglobulin (Ig), such as those described above.

Nucleic acid constructs containing the CTLA4 nucleotide sequences according to the present invention can be transfected into cells described herein that can be used to produce transgenic animals via any technique known to one skilled in the art. In particular, the CTLA4 nucleotide sequences of the present invention can be targeted to a specific location in the genome of the host cell, randomly inserted into the genome of the host cell or otherwise housed in the host cell in such a way to allow heritable transmission of the CTLA4 sequences described herein.

In another embodiment, the nucleic acid construct contains a regulatory sequence operably linked to the CTLA4 sequence. In one embodiment, the regulatory sequence can be a promoter sequence. In one embodiment, the promoter can be a regulateable promoter. In such systems, drugs, for example, can be used to regulate whether the CTLA4 peptide of the present invention is expressed in the animal, tissue or organ. For example, expression can be prevented while the organ or tissue is part of the pig, but expression induced once the pig has been transplanted to the human for a period of time to overcome the cellular immune response. In addition, the level of expression can be controlled by a regulateable promoter system to ensure that immunosuppression of the recipient's immune system does not occur. The regulateable promoter system can be selected from, but not limited to, the following gene systems:

a metallothionein promoter, inducible by metals such as copper (see Lichtlen and Schaffner (2001) The "metal transcription factor" MTF-1: biological facts and medical implications Swiss Med Wkly. 131(45-46):647-52);

a tetracycline-regulated system (see Imhof et al. (2000) A regulatory network for the efficient control of transgene expression. J Gene Med. 2(2):107-16);

an ecdysone-regulated system (see Saez et al. (2000) Identification of ligands and coligands for the ecdysone-regulated gene switch. Proc Natl Acad Sci USA. 97(26):14512-7);

a cytochrome P450 inducible promoter, such as the CYP1A1 promoter (see Fujii-Kuriyama et al. (1992) Regulation of CYP1A1 expression. FASEB J. 6(2): 706-10);

a mifepristone inducible system (see Sirin and Park (2003) Regulating gene expression using self-inactivating lentiviral vectors containing the mifepristone-inducible system. Gene. 323:67-77);

a coumarin-activated system (see Zhao et al. (2003) A coumermycin/novobiocin-regulated gene expression system. Hum Gene Ther. 14(17):1619-29);

a macrolide inducible system (responsive to macrolide antibiotics such as rapamycin, erythromycin, clarithromycin, and roxithromycin) (see Weber et al. (2002) Macrolide-based transgene control in mammalian cells and mice. Nat. Biotechnol. 20(9):901-7; Wang et al. (2003) Single HSV-amplicon vector mediates drug-induced gene expression via dimerizer system. Mol Ther. 7(6):790-800);

an ethanol induced system (see Garoosi et al. (2005 June, Epub April 25) Characterization of the ethanol-inducible alc gene expression system in tomato. J Exp Bot. 56(416):1635-42; Roberts et al. (2005 July) The alc-GR system: a modified alc gene switch designed for use in plant tissue culture. Plant Physiol. 138(3):1259-67);

a streptogramin inducible system (see Fussenegger et al. (2000) Streptogramin-based gene regulation systems for mammalian cells. Nat Biotechnol. 18(11):1203-8)

an electrophile inducible system (see Zhu and Fahl (2001) Functional characterization of transcription regulators that interact with the electrophile response element. Biochem Biophys Res Commun. 289(1):212-9); and a nicotine inducible system (see Malphettes et al. (2005 Jul. 7) A novel mammalian expression system derived from components coordinating nicotine degradation in *arthrobacter nicotinovorans* pAO1. Nucleic Acids Res. 33(12):e107).

In another embodiment, the promoter can be a tissue specific promoter. The tissue specific promoter can be selected from, but not limited to: the albumin promoter (liver-specific; Pinkert et al. (1987) Genes Dev. 1:268-277), lymphoid-specific promoters (Calame and Eaton (1988) Adv. Immunol. 43:235-275), promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), endothelial promoters, pancreas-specific promoters (Edlund et al. (1985) Science 230:912-916), and mammary gland-specific promoters (e.g., milk whey promoter; U.S. Pat. No. 4,873, 316 and European Application Publication No. 264,166). In one particular embodiment, the CTLA4 peptide is not under the control of a neuron-specific promoter.

In a further embodiment, the promoter can be a ubiquitous promoter. Ubiquitous promoters include, but are not limited to the following: viral promoters like CMV, SV40. Suitable promoters also include β-Actin promoter, γ-actin promoter, GAPDH promoters, H$_2$K, ubiquitin and the rosa promoter.

In still further embodiments, the nucleic acid construct or vector can contain a selectable marker gene to identify cells that express the CTLA4 peptide. In one embodiment, the selectable maker gene can be the neomycin-resistance gene. In another embodiment, the selectable marker can be green fluorescent protein.

In another embodiment, the nucleic acid construct or vector can contain gene enhancers. Representative, non-limiting examples of gene-enhancers include CMV-E, pdx-1, TIE-2. Tissue specific expression can be imparted by this gene enhancer alone or in combination with a tissue specific promoter.

In a further aspect of the present invention, CTLA4 transgenic pigs have also been genetically modified to eliminate functional expression of the alpha-1,3-galactosyl-transferase ($\alpha(1,3)$GT) gene (see, for example, PCT publication No. WO 04/028243 by Revivicor, Inc.). In one embodiment, CTLA4 transgenic pigs can be further genetically modified to knockout both alleles of the $\alpha(1,3)$GT gene. In another embodiment, pigs that lack functional expression of $\alpha(1,3)$GT can be further genetically modified to express CTLA4 according to the materials and methods described herein. These animals can be used as a source of tissue and/or organs for transplantation therapy. A pig embryo prepared in this manner or a cell line developed therefrom can also be used in cell-transplantation therapy.

Expression Constructs/Vectors

In embodiments of the present invention, recombinant expression vectors or constructs are provided which include nucleic acid fragments that encode the CTLA4 peptides of the present invention. The nucleic acid molecule coding for such proteins can be inserted into an appropriate expression vector, i.e., a vector that contains the necessary elements for the transcription and translation of the inserted protein-encoding sequence. In one embodiment, the expression vector can include a promoter. In another embodiment, the expression vector can include an enhancer and/or intronic sequence. In further embodiments, the nucleic acid constructs or vectors can contain a selectable marker gene. In other embodiments, the expression vectors or constructs can include: 1) a promoter, 2) the nucleic acid sequence according to the present invention, and 3) a polyadenylation signal sequence. The vectors or constructs can be prepared by any method known to one skilled in the art, for example, isolating a restriction fragment of a plasmid vector which expresses the CTLA4 protein or protein construct in, for example, mammalian cells. In one embodiment, the restriction fragment can be free of bacterially derived sequences that are known by one skilled in the art to have deleterious effects on embryo viability and gene expression.

Genes containing nucleotide sequences encoding the CTLA4 domains can be prepared using a variety of techniques known in the art. For example, the nucleotide sequences encoding the CTLA4 peptide or fragment thereof can be produced using PCR generation and/or restriction digestion of cloned genes to generate fragments encoding amino acid sequences having T Cell and C5b-9 inhibitory activities. These fragments can be assembled using PCR fusion or enzymatic ligation of the restriction digestion products (Sambrook, et al., Molecular Cloning: A laboratory manual. 2nd edition. Cold Spring Harbor Press, 1989; Ausubel et al. Current Protocols in Molecular Biology. 1991). Alternatively, any or all of the nucleic acid fragments used to assemble the genes can be synthesized by chemical means. In another embodiment. the nucleotide sequences encoding CTLA4 and/or Ig domains can be produced using PCR generation and/or restriction digestion of cloned genes to generate fragments encoding amino acid sequences having T Cell and C3 inhibitory activities. These fragments also can be assembled using PCR fusion or enzymatic ligation of the restriction digestion products (Sambrook. et al., Molecular Cloning: A laboratory manual. 2nd edition. Cold Spring Harbor Press. 1989; Ausubel et al., Current Protocols in Molecular Biology. 1991).

In another embodiment, recombinant expression vectors which include nucleic acid fragments of the CTLA4 peptide are provided. The nucleic acid molecule coding for such proteins can be inserted into an appropriate expression vector, i.e., a vector that contains the necessary elements for the transcription and translation of the inserted protein-encoding sequence. Example of promoters and enhancers include those derived from Polyoma virus, Adenovirus, Simian Virus 40 (SV40), the Molony murine leukemia virus (MMLV), including the long terminal repeat (MMLV-LTR), and human cytomegalovirus (CMV), including the cvtomegalovirus immediate-early gene I promoter and enhancer are suitable Suitable host vector systems include, but are not limited to, mammalian cell systems infected with virus (e.g. T. vaccinia virus, adenovirus, retroviruses, etc.), mammalian cell systems transfected with plasmids, insect cell systems infected with virus (e.g. baculovirus); microorganisms such as yeast containing yeast expression vectors, or bacteria transformed with bacteriophage DNA, plasmid DNA, or cosmid DNA. Commonly used promoters and enhancers derived from Polyoma virus, Adenovirus, Simian Virus 40 (SV40), the Molony murine leukemia virus (MMLV), including the Iona terminal repeat (MMLV-LTR), and human cytomegalovirus (CMV), including the cvtomegalovirus immediate-early gene I promoter and enhancer are suitable. Eukaryotic promotors-β-Actin & H2 Kb (Fodor et al. PNAS 1994). The terms "vector" and "plasmid" can be used interchangeably. Additional examples of vectors include, phages, autonomously replicating sequences (ARS), centromeres, and other sequences which are able to replicate or be replicated in vitro or in a cell, or to convey a desired nucleic acid segment to a desired location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575), TA Cloning® brand PCR cloning (Invitrogen Corp., Carlsbad, Calif.)) can also be applied to clone a nucleic acid into a vector to be used according to the present invention. The vector can further contain one or more selectable markers to identify cells transformed with the vector, such as the selectable markers and reporter genes described herein.

In accordance with the invention, any vector can be used to construct the CTLA4 containing expression vectors of the invention. In addition, vectors known in the art and those commercially available (and variants or derivatives thereof) can, in accordance with the invention, be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts.

Other vectors of interest include viral origin vectors (M13 vectors, bacterial phage λ vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Vectors for use herein also include prokaryotic expression vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Additional vectors that can be used include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen) and variants or derivatives thereof. Viral vectors can also be used, such as lentiviral vectors (see, for example, WO 03/059923; Tiscornia et al. PNAS 100:1844-1848 (2003)).

Further vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZa, pGAPZ, pGAPZa, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λ gt 11, pTrc99A, pKK223-3, pGEX-1λT, pGEX-2T, pGEX-2TK, pGEX-4T-1, pGEX-4T-2, pGEX-4T-3, pGEX-3x, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2 LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contra1, pSEAP2-Promoter, pSEAP2-Enhancer, pβgal-Basic, pβgal-Control, pβgal-Promoter, pβgal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and TriplEx from Clontech; Lambda ZAP II, pBK-CMV, pBK-RSV, pBluescript II KS +/−,1 pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT,pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Two-hybrid and reverse two-hybrid vectors of interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Promoters

Non limiting examples of promoters that can be operably linked to the CTL4 sequence include mitochondrial 16S rRNA, ribosomal protein L29 (RPL29), H3 histone, family 3B (H3.3B) ($H_3F_3B$), poly(A)-binding protein, insulin, endoglin, PECAM, TIE, ICAM 1, 2, Actin, cytoplasmic 1 (PABPC1), HLA-B associated transcript-1 (D6S81E), surfeit 1 (SURF1), ribosomal protein L8 (RPL8), ribosomal protein L38 (RPL38), catechol-O-methyltransferase (COMT), ribosomal protein S7 (RPS7), heat shock 27 kD protein 1 (HSPB1), eukaryotic translation elongation factor 1 delta (guanine nucleotide exchange protein) (EEF1D), vimentin (VIM), ribosomal protein L41 (RPL41), carboxylesterase 2 (intestine, liver) (CES2), exportin 1 (CRM1, yeast, homolog) (XPO1), ubiquinol-cytochrome c reductase hinge protein (UQCRH), Glutathione peroxidase 1 (GPX1), ribophorin II (RPN2), Pleckstrin and Sec7 domain protein (PSD), human cardiac troponin T, proteasome (prosome, macropain) subunit, beta type, 5 (PSMB5), cofilin 1 (non-muscle) (CFL1), seryl-tRNA synthetase (SARS), catenin (cadherin-associated protein), beta 1 (88 kD) (CTNNB1), Duffy blood group (FY), erythrocyte membrane protein band 7.2 (stomatin) (EPB72), Fas/Apo-1, LIM and SH3 protein 1 (LASP1), accessory proteins BAP31/BAP29 (DXS1357E), nascent-polypeptide-associated complex alpha polypeptide (NACA), ribosomal protein L18a (RPL18A), TNF receptor-associated factor 4 (TRAF4), MLN51 protein (MLN51), ribosomal protein L11 (RPL11), Poly(rC)-binding protein 2 (PCBP2), thioredoxin (TXN), glutaminyl-tRNA synthetase (QARS), testis enhanced gene transcript (TEGT), prostatic binding protein (PBP), signal sequence receptor, beta (translocon-associated protein beta) (SSR2), ribosomal protein L3 (RPL3), centrin, EF-hand protein,2 (CETN2), heterogeneous nuclear ribonucleoprotein K (HNRPK), glutathione peroxidase 4 (phospholipid hydroperoxidase) (GPX4), fusion, derived from t(12; 16) malignant liposarcoma (FUS), ATP synthase, H+ transporting, mitochondrial F0 complex, subunit c (subunit 9), isoform 2 (ATP5G2), ribosomal protein S26 (RPS26), ribosomal protein L6 (RPL6), ribosomal protein S18 (RPS18), serine (or cysteine) proteinase inhibitor, Glade A (alpha-1 antiproteinase, antitrypsin), member 3 (SERPINA3), dual specificity phosphatase 1 (DUSP1), peroxiredoxin 1 (PRDX1), epididymal secretory protein (19.5 kD) (HE1), ribosomal protein S8 (RPS8), translocated promoter region (to activated MET oncogene) (TPR), ribosomal protein L13 (RPL13), SON DNA binding protein (SON), ribosomal prot L19 (RPL19), ribosomal prot (homolog to yeast S24), CD63 antigen (melanoma 1 antigen) (CD63), protein tyrosine phosphatase, non-receptor type 6 (PTPN6), eukaryotic translation elongation factor 1 beta 2 (EEF1B2), ATP synthase, H+ transporting, mitochondrial F0 complex, subunit b, isoform 1 (ATP5F1), solute carrier family 25 (mitochondrial carrier; phosphate carrier), member 3 (SLC25A3), tryptophanyl-tRNA synthetase (WARS), glutamate-ammonia ligase (glutamine synthase) (GLUL), ribosomal protein L7 (RPL7), interferon induced transmembrane protein 2 (1-8D) (IFITM2), tyrosine 3-monooxygenase/tryptophan 5-monooxygenase activation protein, beta polypeptide (YWHAB), Casein kinase 2, beta polypeptide (CSNK2B), ubiquitin A-52 residue ribosomal protein fusion product 1 (UBA52), ribosomal protein L13a (RPL13A), major histocompatibility complex, class I, E (HLA-E), jun D proto-oncogene (JUND), tyrosine 3-monooxygenase/tryptophan 5-monooxygenase activation protein, theta polypeptide (YWHAQ), ribosomal protein L23 (RPL23), Ribosomal protein S3 (RPS3), ribosomal protein L17 (RPL17), filamin A, alpha (actin-binding protein-280) (FLNA), matrix Gla protein (MGP), ribosomal protein L35a (RPL35A), peptidylprolyl isomerase A (cyclophilin A) (PPIA), villin 2 (ezrin) (VIL2), eukaryotic translation elongation factor 2 (EEF2), jun B proto-oncogene (JUNB), ribosomal protein S2 (RPS2), cytochrome c oxidase subunit VIIc (COX7C), heterogeneous nuclear ribonucleoprotein L (HNRPL), tumor protein, translationally-controlled 1 (TPT1), ribosomal protein L31 (RPL31), cytochrome c oxidase subunit VIIa polypeptide 2 (liver) (COX7A2), DEAD/H (Asp-Glu-Ala-Asp/His) box polypeptide 5 (RNA helicase, 68 kD) (DDXS), cytochrome c oxidase subunit VIa polypeptide 1 (COX6A1), heat shock 90 kD protein 1, alpha (HSPCA), Sjogren syndrome antigen B (autoantigen La) (SSB), lactate dehydrogenase B (LDHB), high-mobility group (nonhistone chromosomal) protein 17 (HMG17), cytochrome c oxidase subunit VIc (COX6C), heterogeneous nuclear ribonucleoprotein A1 (HNRPA1), aldolase A, fructose-bisphosphate (ALDOA), integrin, beta 1 (fibronectin receptor, beta polypeptide, antigen CD29 includes MDF2, MSK12) (ITGB1), ribosomal protein S11 (RPS11), small nuclear ribonucleoprotein 70 kD polypeptide (RN antigen) (SNRP20), guanine nucleotide binding protein (G protein), beta polypeptide 1 (GNB1), heterogeneous nuclear ribonucleoprotein A1 (HNRPA1), calpain 4, small subunit (30K) (CAPN4), elongation factor TU (N-terminus)/X03689, ribosomal protein L32 (RPL32), major histocompatibility complex, class II, DP alpha 1 (HLA-DPA1), superoxide dismutase 1, soluble (amyotrophic lateral sclerosis 1 (adult)) (SOD1), lactate dehydrogenase A (LDHA), glyceraldehyde-3-phosphate dehydrogenase (GAPD), Actin, beta (ACTB), major histocompatibility complex, class II, DP alpha (HLA-DRA), tubulin, beta polypeptide (TUBB), metallothionein 2A (MT2A), phosphoglycerate kinase 1 (PGK1), KRAB-associated protein 1 (TIF1B), eukaryotic translation initiation factor 3, subunit 5 (epsilon, 47 kD) (EIF3S5), NADH dehydrogenase (ubiquinone) 1 alpha subcomplex, 4 (9 kD, MLRQ) (NDUFA4), chloride intracellular channel 1 (CLIC1), adaptor-related protein complex 3, sigma 1 subunit (AP3S1), cytochrome c oxidase subunit IV (COX4), PDZ and LIM domain 1 (elfin) (PDLIM1), glutathione-S-transferase like; glutathione transferase omega (GSTTLp28), interferon stimulated gene (20 kD) (ISG20), nuclear factor I/B (NFIB), COX10 (yeast) homolog, cytochrome c oxidase assembly protein (heme A: farnesyltransferase), conserved gene amplified in osteosarcoma (OS4), deoxyhypusine synthase (DHPS), galactosidase, alpha (GLA), microsomal glutathione S-transferase 2 (MGST2), eukaryotic translation initiation factor 4 gamma, 2 (EIF4G2), ubiquitin carrier protein E2-C (UBCH$_{10}$), BTG family, member 2 (BTG2), B-cell associated protein (REA), COPS subunit 6 (MOV34 homolog, 34 kD) (MOV34-34 KD), ATX1 (antioxidant protein 1, yeast) homolog 1 (ATOX1), acidic protein rich in leucines (SSP29), poly(A)-binding prot (PABP) promoter region, selenoprotein W, 1 (SEPW1), eukaryotic translation initiation factor 3, subunit 6 (48 kD) (EIF3S6), carnitine palmitoyltransferase I, muscle (CPT1B), transmembrane trafficking protein (TMP21), four and a half LIM domains 1 (FHL1), ribosomal protein S28 (RPS28), myeloid leukemia factor 2 (MLF2), neurofilament triplet L prot/U57341, capping protein (actin filament) muscle Z-line, alpha 1 (CAPZA1), 1-acylglycerol-3-phosphate O-acyltransferase 1 (lysophosphatidic acid acyltransferase, alpha) (AGPAT1), inositol 1,3,4-triphosphate 5/6 kinase (ITPK1), histidine triad nucleotide-binding protein (HINT), dynamitin (dynactin complex 50 kD subunit) (DCTN-50), actin related protein 2/3 complex, subunit 2 (34 kD) (ARPC2), histone deacetylase 1 (HDAC1), ubiquitin B, chitinase 3-like 2 (CHI3L2), D-dopachrome tautomerase (DDT), zinc finger protein 220 (ZNF220), sequestosome 1 (SQSTM1), cystatin B (stefin B) (CSTB), eukaryotic translation initiation factor 3, subunit 8 (110 kD) (EIF3S8), chemokine (C—C motif) receptor 9 (CCR9), ubiquitin specific protease 11 (USP11), laminin receptor 1 (67 kD, ribosomal protein SA) (LAMR1), amplified in osteosarcoma (OS-9), splicing factor 3b, subunit 2, 145 kD (SF3B2), integrin-linked kinase (ILK), ubiquitin-conjugating enzyme E2D 3 (homologous to yeast UBC4/5) (UBE2D3), chaperonin containing TCP1, subunit 4 (delta) (CCT4), polymerase (RNA) II (DNA directed) polypeptide L (7.6 kD) (POLR2L), nuclear receptor co-repressor 2 (NCOR2), accessory proteins BAP31/BAP29 (DXS1357E, SLC6A8), 13 kD differentiation-associated protein (L0055967), Tax1 (human T-cell leukemia virus type I) binding protein 1 (TAX1BP1), damage-specific DNA binding protein 1 (127 kD) (DDB1), dynein, cytoplasmic, light polypeptide (PIN), methionine aminopeptidase; eIF-2-associated p67 (MNPEP), G protein pathway suppressor 2 (GPS2), ribosomal protein L21 (RPL21), coatomer protein complex, subunit alpha (COPA), G protein pathway suppressor 1 (GPS1), small nuclear ribonucleoprotein D2 polypeptide (16.5 kD) (SNRPD2), ribosomal protein S29 (RPS29), ribosomal protein S10 (RPS10), ribosomal proteinS9 (RPS9), ribosomal protein S5 (RPS5), ribosomal protein L28 (RPL28), ribosomal protein L27a (RPL27A), protein tyrosine phosphatase type IVA, member 2 (PTP4A2), ribosomal prot L36 (RPL35), ribosomal protein L10a (RPL10A), Fc fragment of IgG, receptor, transporter, alpha (FCGRT), maternal G10 transcript (G10), ribosomal protein L9 (RPL9), ATP synthase, H+ transporting, mitochondrial F0 complex, subunit c (subunit 9) isoform 3 (ATP5G3), signal recognition particle 14 kD (homologous Alu RNA-binding protein) (SRP14), mutL (E. coli) homolog 1 (colon cancer, nonpolyposis type 2) (MLH1), chromosome 1q subtelomeric sequence D1S553./U06155, fibromodulin (FMOD), amino-terminal enhancer of split (AES), Rho GTPase activating protein 1 (ARHGAP1), non-POU-domain-containing, octamer-binding (NONO), v-raf murine sarcoma 3611 viral oncogene homolog 1 (ARAF1), heterogeneous nuclear ribonucleoprotein A1 (HNRPA1), beta 2-microglobulin (B2M), ribosomal protein S27a (RPS27A), bromodomain-containing 2 (BRD2), azoospermia factor 1 (AZF1), upregulated by 1,25 dihydroxyvitamin D-3 (VDUP1), serine (or cysteine) proteinase inhibitor, Glade B (ovalbumin), member 6 (SERPINB6), destrin (actin depolymerizing factor) (ADF), thymosin beta-10 (TMSB10), CD34 antigen (CD34), spectrin, beta, non-erythrocytic 1 (SPTBN1), angio-associated, migratory cell protein (AAMP), major histocompatibility complex, class I, A (HLA-A), MYC-associated zinc finger protein (purine-binding transcription factor) (MAZ), SET translocation (myeloid leukemia-associated) (SET), paired box gene(aniridia, keratitis) (PAX6), zinc finger protein homologous to Zfp-36 in mouse (ZFP36), FK506-binding protein 4 (59 kD) (FKBP4), nucleosome assembly protein 1-like 1 (NAP1L1), tyrosine 3-monooxygenase/tryptophan 5-monooxygenase activation protein, zeta polypeptide (YWHAZ), ribosomal protein S3A (RPS3A), ADP-ribosylation factor 1, ribosomal protein S19 (RPS19), transcription elongation factor A (SII), 1 (TCEA1), ribosomal protein S6 (RPS6), ADP-ribosylation factor 3 (ARF3), moesin (MSN), nuclear factor of kappa light polypeptide gene enhancer in B-cells inhibitor, alpha (NFKBIA), complement component 1, q subcomponent binding protein (C1QBP), ribosomal protein S25 (RPS25), clusterin (complement lysis inhibitor, SP-40,40, sulfated glycoprotein 2, testosterone-repressed prostate message 2, apolipoprotein J) (CLU), nucleolin (NCL), ribosomal protein S16 (RPS16), ubiquitin-activating enzyme E1 (A1S9T and BN75 temperature sensitivity complementing) (UBE1), lectin, galactoside-binding, soluble, 3 (galectin 3) (LGALS3), eukaryotic translation elongation factor 1 gamma (EEF1G), pim-1 oncogene (PIM1), 5100 calcium-binding protein A10 (annexin II ligand,calpactin I, light polypeptide (p11)) (S100A10), H2A histone family, member Z (H2AFZ), ADP-ribosylation factor 4 (ARF4) (ARF4), ribosomal protein L7a (RPL7A), major histocompatibility complex, class II, DQ alpha 1 (HLA-DQA1), FK506-binding protein 1A (12 kD) (FKBP1A), CD81 antigen (target of antiproliferative antibody 1) (CD81), ribosomal protein S15 (RPS15), X-box binding protein 1 (XBP1), major histocompatibility complex, class II, DN alpha (HLA-DNA), ribosomal protein S24 (RPS24), leukemia-associated phosphoprotein p18 (stathmin) (LAP18), myosin, heavy polypeptide 9, non-muscle (MYH9), casein kinase 2, beta polypeptide (CSNK2B), fucosidase, alpha-L-1, tissue (FUCA1), diaphorase (NADH) (cytochrome b-5 reductase) (DIA1), cystatin C (amyloid angiopathy and cerebral hemorrhage) (CST3), ubiquitin C (UBC), ubiquinol-cytochrome c reductase binding protein (UQCRB), prothymosin, alpha (gene sequence 28) (PTMA), glutathione S-transferase pi (GSTP1), guanine nucleotide binding protein (G protein), beta polypeptide 2-like 1 (GNB2L1), nucleophosmin (nucleolar phosphoprotein B23, numatrin) (NPM1), CD3E antigen, epsilon polypeptide (TiT3 complex) (CD3E), calpain 2, (m/II) large subunit (CAPN2), NADH dehydrogenase (ubiquinone) flavoprotein 2 (24 kD) (NDUFV2), heat shock 60 kD protein 1 (chaperonin) (HSPD1), guanine nucleotide binding protein (G protein), alpha stimulating activity polypeptide 1 (GNAS1), clathrin, light polypeptide (Lca) (CLTA), ATP synthase, H+ transporting, mitochondrial F1 complex, beta polypeptide, calmodulin 2 (phosphorylase kinase, delta) (CALM2), actin, gamma 1 (ACTG1), ribosomal protein S17 (RPS17), ribosomal protein, large, P1 (RPLP1), ribosomal protein, large, P0 (RPLP0), thymosin, beta 4, X chromosome (TMSB4X), heterogeneous nuclear ribonucleoprotein C(C1/C2) (HNRPC), ribosomal protein L36a (RPL36A), glucuronidase, beta (GUSB), FYN oncogene related to SRC, FGR, YES (FYN), prothymosin, alpha (gene sequence 28) (PTMA), enolase 1, (alpha) (ENO1), laminin receptor 1 (67 kD, ribosomal protein SA) (LAMR1), ribosomal protein S14 (RPS14), CD74 antigen (invariant polypeptide of major histocompatibility complex, class II antigen-associated), esterase D/formylglutathione hydrolase (ESD), H3 histone, family 3A (H3F3A), ferritin, light polypeptide (FTL), Sec23 (S. cerevisiae) homolog A (SEZ23A), actin, beta (ACTB), presenilin 1 (Alzheimer disease 3) (PSEN1), interleukin-1 receptor-associated kinase 1 (IRAK1), zinc finger protein 162 (ZNF162), ribosomal protein L34 (RPL34), beclin 1 (coiled-coil, myosin-like BCL2-interacting protein) (BECN1), phosphatidylinositol 4-kinase, catalytic, alpha polypeptide (PIK4CA), IQ motif containing GTPase activating protein 1 (IQGAP1), signal transducer and activator of transcription 3 (acute-phase response factor) (STAT3), heterogeneous nuclear ribonucleoprotein F (HNRPF), putative translation initiation factor (SUI1), protein translocation complex beta (SEC61B), ras homolog gene family, member A (ARHA), ferritin, heavy polypeptide 1 (FTH1), Rho GDP dissociation inhibitor (GDI) beta (ARHGDIB), H2A histone family, member O (H2AFO), annexin A11 (ANXA11), ribosomal protein L27 (RPL27), adenylyl cyclase-associated protein (CAP), zinc finger protein 91 (HPF7, HTF10) (ZNF91), ribosomal protein L18 (RPL18), farnesyltransferase, CAAX box, alpha (FNTA), sodium channel, voltage-gated, type I, beta polypeptide (SCN1B), calnexin (CANX), proteolipid protein 2 (colonic epithelium-enriched) (PLP2), amyloid beta (A4) precursor-like protein 2 (APLP2), Voltage-dependent anion channel 2, proteasome (prosome, macropain) activator subunit 1 (PA28 alpha) (PSME1), ribosomal prot L12 (RPL12), ribosomal protein L37a (RPL37A), ribosomal protein S21 (RPS21), proteasome (prosome, macropain) 26S subunit, ATPase, 1 (PSMC1), major histocompatibility complex, class II, DQ beta 1 (HLA-DQB1), replication protein A2 (32 kD) (RPA2), heat shock 90 kD protein 1, beta (HSPCB), cytochrome c oxydase subunit VIII (COX8), eukaryotic translation elongation factor 1 alpha 1 (EEF1A1), SNRPN upstream reading frame (SNURF), lectin, galactoside-binding, soluble, 1 (galectin 1)

(LGALS1), lysosomal-associated membrane protein 1 (LAMP1), phosphoglycerate mutase 1 (brain) (PGAM1), interferon-induced transmembrane protein 1 (9-27) (IFITM1), nuclease sensitive element binding protein 1 (NSEP1), solute carrier family 25 (mitochondrial carrier; adenine nucleotide translocator), member 6 (SLC25A6), ADP-ribosyltransferase (NAD+; poly (ADP-ribose) polymerase) (ADPRT), leukotriene A4 hydrolase (LTA4H), profilin 1 (PFN1), prosaposin (variant Gaucher disease and variant metachromatic leukodystrophy) (PSAP), solute carrier family 25 (mitochondrial carrier; adenine nucleotide translocator), member 5 (SLC25A5), beta-2 microglobulin, insulin-like growth factor binding protein 7, Ribosomal prot S13, Epstein-Barr Virus Small Rna-Associated prot, Major Histocompatibility Complex, Class I, C X58536), Ribosomal prot S12, Ribosomal prot L10, Transformation-Related prot, Ribosomal prot L5, Transcriptional Coactivator Pc4, Cathepsin B, Ribosomal prot L26, "Major Histocompatibility Complex, Class I X12432", Wilm S Tumor-Related prot, Tropomyosin Tm30 nm Cytoskeletal, Liposomal Protein S4, X-Linked, Ribosomal prot L37, Metallopanstimulin 1, Ribosomal prot L30, Heterogeneous Nuclear Ribonucleoprot K, Major Histocompatibility Complex, Class I, E M21533, Major Histocompatibility Complex, Class I, E M20022, Ribosomal protein L30 Homolog, Heat Shock prot 70 Kda, "Myosin, Light Chain/U02629", "Myosin, Light Chain/U02629", Calcyclin, Single-Stranded Dna-Binding prot Mssp-1, Triosephosphate Isomerase, Nuclear Mitotic Apparatus prot 1, prot Kinase Ht31 Camp-Dependent, Tubulin, Beta 2, Calmodulin Type I, Ribosomal prot S20, Transcription Factor Btf3b, Globin, Beta, Small Nuclear RibonucleoproteinPolypeptide CAlt. Splice 2, Nucleoside Diphosphate Kinase Nm23-H2s, Ras-Related C3 Botulinum Toxin Substrate, activating transcription factor 4 (tax-responsive enhancer element B67) (ATF4), prefoldin (PFDN5), N-myc downstream regulated (NDRG1), ribosomal protein L14 (RPL14), nicastrin (KIAA0253), protease, serine, 11 (IGF binding) (PRSS11), KIAA0220 protein (KIAA0220), dishevelled 3 (homologous to *Drosophila* dsh) (DVL3), enhancer of rudimentary *Drosophila* homolog (ERH), RNA-binding protein gene with multiple splicing (RBPMS),5-aminoimidazole-4-carboxamide ribonucleotide formyltransferase/IMP cyclohydrolase (ATIC), KIAA0164 gene product (KIAA0164), ribosomal protein L39 (RPL39), tyrosine 3 monooxygenase/tryptophan 5-monooxygenase activation protein, eta polypeptide (YWHAH), Ornithine decarboxylase antizyme 1 (OAZ1), proteasome (prosome, macropain) 26S subunit, non-ATPase, 2 (PSMD2), cold inducible RNA-binding protein (CIRBP), neural precursor cell expressed, developmentally down-regulated 5 (NEDD5), high-mobility group nonhistone chromosomal protein 1 (HMG1), malate dehydrogenase 1, NAD (soluble) (MDH1), cyclin I (CCNI), proteasome (prosome, macropain) 26S subunit, non-ATPase, 7 (Mov34 homolog) (PSMD7), major histocompatibility complex, class I, B (HLA-B), ATPase, vacuolar, 14 kD (ATP6S14), transcription factor-like 1 (TCFL1), KIAA0084 protein (KIAA0084), proteasome (prosome, macropain) 26S subunit, non-ATPase, 8 (PSMD8), major histocompatibility complex, class I, A (HIA-A), alanyl-tRNA synthetase (AARS), lysyl-tRNA synthetase (KARS), ADP-ribosylation factor-like 6 interacting protein (ARL61P), KIAA0063 gene product (KIAA0063), actin binding LIM protein 1 (ABLIM), DAZ associated protein 2 (DAZAP2), eukaryotic translation initiation factor 4A, isoform 2 (EIF4A2), CD151 antigen (CD151), proteasome (prosome, macropain) subunit, beta type, 6 (PSMB6), proteasome (prosome, macropain) subunit, beta type, 4 (PSMB4), proteasome (prosome, macropain) subunit, beta type, 2 (PSMB2), proteasome (prosome, macropain) subunit, beta type, 3 (PSMB3), Williams-Beuren syndrome chromosome region 1 (WBSCR1), ancient ubiquitous protein 1 (AUP1), KIAA0864 protein (KIAA0864), neural precursor cell expressed, developmentally down-regulated 8 (NEDD8), ribosomal protein L4 (RPL4), KIAA0111 gene product (KIAA0111), transgelin 2 (TAGLN2), Clathrin, heavy polypeptide (Hc) (CLTC, CLTCL2), ATP synthase, H+ transporting, mitochondrial F1 complex, gamma polypeptide 1 (ATP5C1), calpastatin (CAST), MORF-related gene X (KIA0026), ATP synthase, H+ transporting, mitochondrial F1 complex, alpha subunit, isoform 1, cardiac muscle (ATP5A1), phosphatidylserine synthase 1 (PTDSS1), anti-oxidant protein 2 (non-selenium glutathione peroxidase, acidic calcium-independent phospholipase A2) (KIAA0106), KIAA0102 gene product (KIAA0102), ribosomal protein S23 (RPS23), CD164 antigen, sialomucin (CD164), GDP dissociation inhibitor 2 (GDI2), enoyl Coenzyme A hydratase, short chain, 1, mitochondrial (ECHS1), eukaryotic translation initiation factor 4A, isoform 1 (EIF4A1), cyclin D2 (CCND2), heterogeneous nuclear ribonucleoprotein U (scaffold attachment factor A) (HNRPU), APEX nuclease (multifunctional DNA repair enzyme) (APEX), ATP synthase, H+ transporting, mitochondrial F0 complex, subunit c (subunit 9), isoform 1 (ATP5G1), myristoylated alanine-rich protein kinase C substrate (MARCKS, 80K-L) (MACS), annexin A2 (ANXA2), similar to *S. cerevisiae* RER1 (RER1), hyaluronoglucosaminidase 2 (HYAL2), uroplakin 1A (UPK1A), nuclear pore complex interacting protein (NPIP), karyopherin alpha 4 (importin alpha 3) (KPNA4), ant the gene with multiple splice variants near HD locus on 4p16.3 (RES4-22).

Selectable Marker Genes

In other embodiments, the vectors or contructs encoding the CTLA4 peptides can also include a selectable marker gene. In one embodiments, the cells can be assayed functionally to determine whether successful targeting has occurred. In another embodiment, the cells can be analyzed by restriction analysis, electrophoresis, Southern analysis, polymerase chain reaction, sequencing or another technique known in the art to determine whether appropriate integration of the DNA encoding the CTLA4 peptide has occurred.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See Song et al., Proc. Nat'l Acad. Sci. U.S.A. 84:6820-6824 (1987). See also Sambrook et al., Molecular Cloning—A Laboratory Manual, Cold Spring Harbor Laboratory, Cold Spring Harbor, N.Y. (1989), see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo), Southern, P., and P. Berg, J. Mol. Appl. Genet. 1:327-341 (1982); and the hygromycin resistance gene (hyg), Nucleic Acids Research 11:6895-6911 (1983), and Te Riele et al., Nature 348:649-651 (1990). Other selectable marker genes include: acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. Nos. 6,080,576; 6,136,566; Niwa, et al., *J. Biochem.* 113: 343-349 (1993); and Yoshida, et al., *Transgenic Research*, 4:277-287 (1995)).

Additional selectable marker genes useful in this invention, for example, are described in U.S. Pat. Nos. 6,319,669; 6,316,181; 6,303,373; 6,291,177; 6,284,519; 6,284,496; 6,280,934; 6,274,354; 6,270,958; 6,268,201; 6,265,548; 6,261,760; 6,255,558; 6,255,071; 6,251,677; 6,251,602; 6,251,582; 6,251,384; 6,248,558; 6,248,550; 6,248,543; 6,232,107; 6,228,639; 6,225,082; 6,221,612; 6,218,185; 6,214,567; 6,214,563; 6,210,922; 6,210,910; 6,203,986; 6,197,928; 6,180,343; 6,172,188; 6,153,409; 6,150,176; 6,146,826; 6,140,132; 6,136,539; 6,136,538; 6,133,429; 6,130,313; 6,124,128; 6,110,711; 6,096,865; 6,096,717; 6,093,808; 6,090,919; 6,083,690; 6,077,707; 6,066,476; 6,060,247; 6,054,321; 6,037,133; 6,027,881; 6,025,192; 6,020,192; 6,013,447; 6,001,557; 5,994,077; 5,994,071; 5,993,778; 5,989,808; 5,985,577; 5,968,773; 5,968,738; 5,958,713; 5,952,236; 5,948,889; 5,948,681; 5,942,387; 5,932,435; 5,922,576; 5,919,445; and 5,914,233. Combinations of selectable markers can also be used.

Transfection

The CTLA4 nucleotide sequences, optionally housed in constructs or vectors can be transfected into host cells by any means known to one skilled in the art. The nucleotides can be transfected via biological, chemical or mechanical means. In one embodiment, the nucleotides can be transfected via electroporation. Electroporation uses electricity to increase the permeability of the eukaryotic cell membrane, allowing foreign DNA to pass easily inside. In another embodiment the nucleotides can be transfected via lipofection. Lipofection, which delivers DNA by fusing to the cell and allowing its DNA payload to be absorbed into the cell, has a similar problem and is more limited in the DNA it can deliver. In further embodiments, the nucleotides can be transfected via virus vector, gene guns, and/or microinjection.

Targeted Insertion

In another embodiment, the insertion of the CTLA4 peptide is targeted to a specific gene locus through homologous recombination in porcine cells. The porcine cells can then be used as nuclear donors to clone (via nuclear transfer) pigs that express the CTLA4 peptide at a known location within the genome of the pig.

Homologous recombination provides a precise mechanism for targeting defined modifications to genomes in living cells (see, for example, Vasquez K M et al. (2001) PNAS USA 98(15):8403-8410). A primary step in homologous recombination is DNA strand exchange, which involves a pairing of a DNA duplex with at least one DNA strand containing a complementary sequence to form an intermediate recombination structure containing heteroduplex DNA (see, for example, Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (see, for example, Hsieh et al. (1990) Genes and Development 4: 1951; Rao et al., (1991) PNAS 88:2984)) and, when two complementary DNA strands pair with a DNA duplex, a classical Holliday recombination joint or chi structure (Holliday, R. (1964) Genet. Res. 5: 282) can form, or a double-D loop ("Diagnostic Applications of Double-D Loop Formation" U.S. Pat. No. 5,273,881). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (see, for example, Genes, 3rd Ed. (1987) Lewin, B., John Wiley, New York, N.Y.; Lopez et al. (1987) Nucleic Acids Res. 15: 5643). Whether by the mechanism of breakage and rejoining or by the mechanism(s) of gene conversion, formation of heteroduplex DNA at homologously paired joints can serve to transfer genetic sequence information from one DNA molecule to another.

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51: 503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al. (1987) Nature 330:576-578; Thoma and Capecchi, (1987) Cell 51:503-512; Thompson et al. (1989) Cell 56:316-321.

Cells useful for homologous recombination include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc.

The vector construct containing the CTLA4 peptide of the present invention can contain a full or partial sequence of one or more exons and/or introns of the gene targeted for insertion, a full or partial promoter sequence of the gene targeted for insertion, or combinations thereof. In one embodiment of the invention, the nucleic acid sequence of the CTLA4 peptide containing construct comprises a first nucleic acid sequence region homologous to a first nucleic acid sequence region of the gene targeted for insertion, and a second nucleic acid sequence region homologous to a second nucleic acid sequence region of the gene targeted for insertion. The orientation of the vector construct should be such that the first nucleic acid sequence is upstream of the second nucleic acid sequence and the CTLA4 construct should be therebetween.

A nucleic acid sequence region(s) can be selected so that there is homology between the CTLA4 containing vector construct sequence(s) and the gene of interest. The construct sequences can be isogenic sequences with respect to the target sequences. The nucleic acid sequence region of the construct may correlate to any region of the gene provided that it is homologous to the gene. A nucleic acid sequence is considered to be "homologous" if it is at least about 90% identical, preferably at least about 95% identical, or most preferably, about 98% identical to the nucleic acid sequence. Furthermore, the 5' and 3' nucleic acid sequences flanking the selectable marker should be sufficiently large to provide complementary sequence for hybridization when the construct is introduced into the genomic DNA of the target cell. For example, homologous nucleic acid sequences flanking the selectable marker gene should be at least about 500 bp, preferably, at least about 1 kilobase (kb), more preferably about 2-4 kb, and most preferably about 3-4 kb in length. In one embodiment, both of the homologous nucleic acid sequences flanking the selectable marker gene of the construct should be should be at least about 500 bp, preferably, at least about 1 kb, more preferably about 2-4 kb, and most preferably about 3-4 kb in length.

Another type of DNA sequence can be a cDNA sequence provided the cDNA is sufficiently large. Each of the flanking nucleic acid sequences used to make the construct is preferably homologous to one or more exon and/or intron regions, and/or a promoter region.

Each of these sequences is different from the other, but may be homologous to regions within the same exon and/or intron. Alternatively, these sequences may be homologous to regions within different exons and/or introns of the gene. The two flanking nucleic acid sequences of the construct can be homologous to two sequence regions of the same or different introns of the gene of interest. In addition, isogenic DNA can be used to make the construct of the present invention. Thus, the nucleic acid sequences obtained to make the construct can be obtained from the same cell line as that being used as the target cell.

Alternatively, a targeting construct can be used in which a single region of homology is present. In such constructs, a single homologous cross-over event produces an insertion within the homolgous regions. This construct can either be supplied circular or is linear and spontaneously circularized within the cell via natural processes (Hasty P, Rivera-Perez J, Chang C, Bradley A. Target frequency and integration pattern for insertion and replacement vectors in embryonic stem cells. Mol Cell Biol. 1991 September; 11(9):4509-17).

In one embodiment of the present invention, homologous recombination is used to insert a CTLA4 containing expression vector operably linked to a promoter into the genome of a cell, such as a fibroblast. The DNA can comprise at least a portion of the gene at the particular locus with introduction of the expression vector into at least one, optionally both copies, of the targeted gene.

Alternatively, a CTLA4 containing expression vector lacking a promoter can be inserted into an endogenous gene. The insertion allows expression of the promoterless vector to be driven by the endogenous gene's associated promoter. In one embodiment, the vector is inserted into the 3' non-coding region of a gene. In a particular aspect of the invention, the vector is inserted into a tissue specific or physiologically specific gene. For example, hepatocyte specific expression is provided by targeting an endogenous gene that is expressed in every hepatocyte at the desired level and temporal pattern. In another embodiment, a targeting vector is assembled such that the CTLA4 containing vector can be inserted into a single allele of a housekeeping gene.

In one embodiment a CTLA4 template containing vector is inserted into a targeted housekeeping gene within an intron of the target housekeeping gene. In one sub-embodiment, the target housekeeping gene is prevented from being translated by insertion of a promoterless engineered CTLA4 template that contains multiple stop codons in the 3' end of the construct within an intron of the target gene. Using this 'promoter-trap' strategy, the CTLA4 construct is spliced into the chromosome, potentially in frame with the upstream of the exon comprising the target gene. This results in the expression of the CTLA4 template prior to the targeted housekeeping gene. In some embodiments, the CTLA4 template expression concomitantly inhibits expression of the housekeeping gene due to the presence of multiple stop codons downstream of the CTLA4 template. Furthermore, expression of the CTLA4 template is under control of the endogenous housekeeping gene promoter. For such a "promoter-trap" strategy, a housekeeping gene targeting construct is designed which contains a sequence with homology to an intron sequence of the target housekeeping gene, a downstream intron splice acceptor signal sequence comprising the AG dinucleotide splice acceptor site, a promoterless CTLA4 template engineered to contain multiple stop codons 3' of the CTLA4 template, the intron splice donor signal sequence comprising the GT dinucleotide splice donor site for splicing the engineered CTLA4 template to the immediate downstream exon, and additional sequence with homology to the intron sequence of the target gene to aid with annealing to the target gene.

In another embodiment, the 'promoter trap' strategy is used to insert the CTLA4 containing vector in the target housekeeping gene by replacing an endogenous housekeeping exon with an in-frame, promoterless CTLA4 containing vector. The CTLA4 \containing vector is spliced into the chromosome and results in the expression of the CTLA4 peptide and concomitant inhibited expression of the full-length target housekeeping gene. Further, the CTLA4 gene is under the control of the housekeeping gene's associated promoter.

This 'promoter trap' gene targeting construct may be designed to contain a sequence with homology to the target housekeeping gene 3' intron sequence upstream of the start codon, the upstream intron splice acceptor sequence comprising the AG dinucleotide splice acceptor site, a Kozak consensus sequence, a promoterless CTLA4 containing vector containing e.g., a polyA termination sequence, a splice donor sequence comprising the GT dinucleotide splice donor site from a intron region downstream of the start codon, and a sequence with 5' sequence homology to the downstream intron. It will be appreciated that the method may be used to target any exon within the targeted housekeeping gene.

In one embodiment, the DNA is randomly inserted into the chromosome and is designed to signal its presence via the activation of a reporter gene, which both mimics the expression of the endogenous gene and potentially mutates the locus. By selecting in cell culture those cells in which the reporter gene has been activated, animals can be generated far more quickly than by conventional gene mutation because there is no need to target each gene separately.

In another embodiment, the transgene expression of a vector containing CTLA4 can be operably linked to a promoter through the use of an Epstein-Barr Virus (EBV) mini-chromosome vector. A number of papers discuss the use of EBV mini-chromosomes for transgene expression of vectors (see, for example, Saeki Y et al. (1998) Human Gene Therapy 10:2787-2794; Saeki Y et al. (1998) Gene Therapy 5:1031-1037).

In embodiments of the present invention, linearized vectors or synthetic oligonucleotides that contain 5' and 3' recombination arms and a DNA template encoding CTLA4 peptides of the present invention are provided. In one embodiment, these targeting constructs can be inserted into an exon or intron of an endogenous gene without disrupting the expression of the endogenous gene. In another embodiment, the CTLA4 gene is embedded within a self-contained, sequence that is capable of functional as an intron. The CTLA4-containing intron is then inserted into an exon of an endogenous gene such that the resulting recombination allows CTLA4 expression under the control of the endogenous gene regulatory elements and does not prevent expression and translation of the same endogenous gene.

In another embodiment, the targeting construct can be inserted into a gene and render the gene inactivated, "knockout" the gene. In particular embodiments of the present invention, the targeting constructs produced according to the methods described herein can knockout xenoantigenic genes, such as alpha-1,3-galactosyltransferase (such as described in Phelps, et al., Science, 299: pp. 411-414 (2003) or WO 2004/028243).

In another embodiment, CTLA4 transgenic animals of the present invention can also lack genes associated with an adverse immune response in xenotransplantation, such as, for example, α(1,3)GT, CMP—NeuAc hydroxylase (see, for example, PCT Publication No. WO 04/108904), porcine iGb3 synthase (see, for example, PCT Publication No. WO 05/047469) and/or porcine FSM synthetase (see, for example, PCT Publication No. WO 05/111204). In addition, CTLA4 transgenic animals of the present invention, optionally lacking one or more additional genes associated with an adverse immune response, can be modified to express complement inhibiting proteins such as, for example, CD59, DAF (such as human DAF) and/or MCP (CD46). The transgenic animals of the present invention can further be modified to express anticoagulant genes, including, for example, tissue factor pathway inhibitor gene (TFPI), hirudin, thrombomodulin, and CD39. See, for example U.S. Pat. No. 6,423,316. When the second genetic modification involves the addition of a gene, the gene added is not fused to CTLA4 or CTL4 Ig, i.e., the expression product is not a fusion protein. These animals can be used as a source of tissue and/or organs for transplantation therapy. A pig embryo prepared in this manner or a cell line developed therefrom can also be used in cell transplantation therapy.

Random Insertion

In one embodiment, the DNA encoding the CTLA4 sequences described herein, including, but not limited to the CTLA4-Ig constructs, optionally packaged in a vector, can be randomly inserted into the chromosome of a cell. In one embodiment, the DNA encoding the CTLA4 sequences described herein, including, but not limited to the CTLA4-Ig constructs, optionally packaged in a vector, can be designed to include a reporter gene so that the presence of the CTLA4 molecule can be detected via the activation of the reporter gene. Any reporter gene known in the art can be used, such as those disclosed above. By selecting in cell culture those cells in which the reporter gene has been activated, cells can be selected that contain CTLA4. In other embodiments, the DNA encoding the CTLA4 sequences described herein, optionally packaged in a vector, can be introduced into a cell via electroporation. In other embodiments, the DNA encoding the CTLA4 sequences described herein, including, but not limited to the CTLA4-Ig constructs, optionally packaged in a vector, can be introduced into a cell via lipofection. In one embodiment, the electroporation and/or lipofection can be used to transfect fibroblast cells. In a particular embodiment, the transfected fibroblast cells can be used as nuclear donors for nuclear transfer to generate transgenic animals as known in the art and described below.

In one particular embodiment, hDAF can be co-transfect with the DNA encoding the CTLA4 sequences described herein, including, but not limited to the CTLA4-Ig constructs, optionally packaged in a vector. The transfected cells can then be stained for the presence of the hDAF construct, which can optionally be transient. In one embodiment, the DNA encoding the CTLA4 sequences described herein, including, but not limited to the CTLA4-Ig constructs, optionally packaged in a vector, was transfected along with the hDAF construct and thus the hDAF staining can be used to detect the presence of the CTLA4.

Cells that have been stained for the presence of a reporter gene, such as those described above, including, but not limited to hDAF, can then be sorted by FACS to enrich the cell population such that we have a higher percentage of cells that contain the DNA encoding the CTLA4 sequences described herein, including, but not limited to the CTLA4-Ig constructs, optionally packaged in a vector. In other embodiments, the FACS-sorted cells can then be cultured for a peios of time, such as 12, 24, 36, 48, 72, 96 or more hours or for such a time period to allow the DNA to integrate to yield a stable transfected cell population.

Artificial Chromosomes

In one particular embodiment, artificial chromosome (ACs) can be used to accomplish the transfer of CTLA4 genes as described herein into ungulate cells and animals. ACs are not integrated into the host cell genome, but allow for heritable transmission of the genes they contain. ACs permit integration of DNA fragments that contain single or multiple genes. The ACs, therefore, can introduce heterologous DNA into selected cells for production of the gene product encoded by the heterologous DNA. First constructed in yeast in 1983, ACs are man-made linear DNA molecules constructed from essential cis-acting DNA sequence elements that are responsible for the proper replication and partitioning of natural chromosomes (Murray et al. (1983), Nature 301:189-193). A chromosome requires at least three elements to function. Specifically, the elements of an artificial chromosome include at least: (1) autonomous replication sequences (ARS) (having properties of replication origins—which are the sites for initiation of DNA replication), (2) centromeres (site of kinetochore assembly that is responsible for proper distribution of replicated chromosomes at mitosis and meiosis), and (3) telomeres (specialized structures at the ends of linear chromosomes that function to both stabilize the ends and facilitate the complete replication of the extreme termim of the DNA molecule).

In one embodiment, the CTLA4 genes of the present invention can be maintained as an independent unit (an episome) apart from the ungulate chromosomal DNA. For example, episomal vectors contain the necessary DNA sequence elements required for DNA replication and maintenance of the vector within the cell. Episomal vectors are available commercially (see, for example, Maniatis, T. et al., Molecular Cloning, A Laboratory Manual (1982) pp. 368-369). The AC can stably replicate and segregate along side endogenous chromosomes. In an alternative embodiment, the CTLA4 DNA sequences of the present invention can be integrated into the ungulate cell's chromosomes thereby permitting the new information to be replicated and partitioned to the cell's progeny as a part of the natural chromosomes (see, for example, Wigler et al. (1977), Cell 11:223). The AC can be translocated to, or inserted into, the endogenous chromosome of the ungulate cell. Two or more ACs can be introduced to the host cell simultaneously or sequentially.

ACs, furthermore, can provide an extra-genomic locus for targeted integration of megabase size DNA fragments that contain single or multiple genes, including multiple copies of a single gene operatively linked to one promoter or each copy or several copies linked to separate promoters. The ACs can be generated by culturing the cells with dicentric chromosomes (i.e., chromosomes with two centromeres) under such conditions known to one skilled in the art whereby the chromosome breaks to form a minichromosome and formerly dicentric chromosome.

ACs can be constructed from humans (human artificial chromosomes: "HACs"), yeast (yeast artificial chromosomes: "YACs"), bacteria (bacterial artificial chromosomes: "BACs"), bacteriophage P1-derived artificial chromosomes: "PACs") and other mammals (mammalian artificial chromosomes: "MACs"). The ACs derive their name (e.g., YAC, BAC, PAC, MAC, HAC) based on the origin of the centromere. A YAC, for example, can derive its centromere from *S. cerevisiae*. MACs, on the other hand, include an active mammalian centromere while HACs refer to chromosomes that include human centromeres. Furthermore, plant artificial chromosomes ("PLACs") and insect artificial chromosomes can also be constructed. The ACs can include elements derived from chromosomes that are responsible for both replication and maintenance. ACs, therefore, are capable of stably maintaining large genomic DNA fragments. (see also, PCT Publication No. WO 06/047603).

III. Production of Transgenic Animals

Engineered transgenic animals such as ungulates or pigs that express the CTLA4 protein described herein produced using any suitable techniques known in the art. These techniques include, but are not limited to, microinjection, e.g., of pronuclei, sperm-mediated gene transfer, electroporation of ova or zygotes, and/or nuclear transplantation.

In other embodiments, sperm mediated gene transfer can be used to produce the genetically modified ungulates described herein. The methods and compositions described herein to insert CTLA4 genes and/or CTLA4-Ig fusion genes can be used to genetically modify sperm cells via any technique described herein or known in the art. The genetically modified sperm can then be used to impregnate a female recipient via artificial insemination, intracytoplasmic sperm injection or any other known technique. In one embodiment, the sperm and/or sperm head can be incubated with the exogenous nucleic acid for a sufficient time period. Sufficient time periods include, for example, about 30 seconds to about 5 minutes, typically about 45 seconds to about 3 minutes, more typically about 1 minute to about 2 minutes.

The potential use of sperm cells as vectors for gene transfer was first suggested by Brackeff et al., Proc., Natl. Acad. Sci. USA 68:353-357 (1971). This was followed by reports of the production of transgenic mice and pigs after in vitro fertilization of oocytes with sperm that had been incubated by naked DNA (see, for example, Lavitrano et al., Cell 57:717-723 (1989) and Gandolfi et al. Journal of Reproduction and Fertility Abstract Series 4, 10 (1989)), although other laboratories were not able to repeat these experiments (see, for example, Brinster et al. Cell 59:239-241 (1989) and Gavora et al., Canadian Journal of Animal Science 71:287-291 (1991)). Since then, successful sperm mediated gene transfer has been achieved in chicken (see, for example, Nakanishi and Iritani, Mol. Reprod. Dev. 36:258-261 (1993)); mice (see, for example, Maione, Mol. Reprod. Dev. 59:406 (1998)); and pigs (see, for example, Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; issued Apr. 23, 2002; U.S. Patent Publication Nos. 20010044937, published Nov. 22, 2001, and 20020108132, published Aug. 8, 2002).

In other embodiments, intracytoplasmic sperm injection can be used to produce the genetically modified ungulates described herein This can be accomplished by coinserting an exogenous nucleic acid and a sperm into the cytoplasm of an unfertilized oocyte to form a transgenic fertilized oocyte, and allowing the transgenic fertilized oocyte to develop into a transgenic embryo and, if desired, into a live offspring. The sperm can be a membrane-disrupted sperm head or a demembranated sperm head. The coinsertion step can include the substep of preincubating the sperm with the exogenous nucleic acid for a sufficient time period, for example, about 30 seconds to about 5 minutes, typically about 45 seconds to about. 3 minutes, more typically about 1 minute to about 2 minutes. The coinsertion of the sperm and exogenous nucleic acid into the oocyte can be via microinjection. The exogenous nucleic acid mixed with the sperm can contain more than one transgene, to produce an embryo that is transgenic for more than one transgene as described herein. The intracytoplasmic sperm injection can be accomplished by any technique known in the art, see, for example, U.S. Pat. No. 6,376,743.

Any additional technique known in the art may be used to introduce the transgene into animals. Such techniques include, but are not limited to pronuclear microinjection (see, for example, Hoppe, P. C. and Wagner, T. E., 1989, U.S. Pat. No. 4,873,191); retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); cell gun; transfection; transduction; retroviral infection; adenoviral infection; adenoviral.-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Anithals, Intl. Rev. Cytol. 115:171-229. In particular embodiments, the expression of CTLA4 and/or CTLA4-Ig fusion genes in ungulates as described herein, can be accomplished via these techniques.

Microinjection

In another aspect of the present invention, methods are provided to produce transgenic animals expressing CTLA4. In one embodiment, microinjection of the constructs encoding the CTLA4 of the present invention can be used to produce the transgenic animals. In one embodiment, the nucleic acid construct or vector can be microinjection into the pronuclei of the zygote. In one embodiment, the construct or vector can be injected into the male pronuclei of the zygote. In another embodiment, the construct or vector can be injected into the female pronuclei of the zygote. In a further embodiment, the construct or vector can be injected via sperm-mediated gene transfer.

Microinjection of the CTLA4 containing construct or vector if the present invention can include the following steps: superovulation of a donor female; surgical removal of the egg, fertilization of the egg; injection of the transgene transcription unit into the pronuclei of the embryo; and introduction of the transgenic embryo into the reproductive tract of a pseudopregnant host mother, usually of the same species. See for example U.S. Pat. No. 4,873,191, Brinster. et al. 1985. PNAS 82:4438; Hogan, et al., in "Manipulating the Mouse Embryo: A Laboratory Manual". Cold Spring Harbor Laboratory, Cold Spring Harbor, N.Y., 1986. Robertson. 1987. in Robertson. ed. "Teratocarcinomas and Embryonic Stem Cells a Practical Approach" IRL Press, Evnsham. Oxford, England. Pedersen, et al., 1990. "Transgenic Techniques in Mice—A Video Guide", Cold Spring Harbor Laboratory, Cold Spring Harbor. N.Y. Transgenic porcine are routinely produced by the microinjection of a transgene construct or vector into pig embryos. In one embodiment, the presence of the transgene can be detected by isolating genomic DNA from tissue from the tail of each piglet and subjecting about 5 micrograms of this genomic DNA to nucleic acid hybridization analysis with a transgene specific probe. In a particular embodiment, transgenic animals can be produced according to any method known to one skilled in the art, for example, as disclosed in Bleck et al., J. Anim. Sci., 76:3072 [1998]; also described in U.S. Pat. Nos. 6,872,868; 6,066,725; 5,523,226; 5,453,457; 4,873,191; 4,736,866; and/or PCT Publication No. WO/9907829.

In one embodiment, the pronuclear microinjection method can include linking at least approximately 50, 100, 200, 300, 400 or 500 copies of the CTLA4 gene-containing construct or vector of the present invention to a promoter of choice, for example, as disclosed herein, and then the foreign DNA can be injected through a fine glass needle into fertilized eggs. In one embodiment, the DNA can be injected into the male pronucleus of the zygote. Pig ova are opaque and visualization of nuclear structures can be difficult. In one embodiment, the pronuclei or nuclei of pig ova can be visualized after centrifugation, for example, at 15000 g for 3 min. The injection of the pronucleus can be carried out under magnification and use of standard microinjection apparatus. The ova can be held by a blunt holding pipette and the zona pellucida, plasma membrane and pronuclear envelope can be penetrated by an injection pipette. The blunt holding pipette can have a small diameter, for example, approximately 50 um. The injection pipette can have a smaller diameter than the holding pipette, for example, approximately 15 um. DNA integration occurs during replication as a repair function of the host DNA. These eggs, containing the foreign DNA, can then be implanted into surrogate mothers for gestation of the embryo according to any technique known to one skilled in the art.

In some embodiments, pronuclear microinjection can be performed on the zygote 12 hours post fertilization. Uptake of such genes can be delayed for several cell cycles. The consequence of this is that depending on the cell cycle of uptake, only some cell lineages may carry the transgene, resulting in mosaic offspring. If desired, mosaic animals can be bred to form true germline transgenic animals.

Nuclear Transfer

In other embodiments, ungulate cells such as porcine cells containing nucleic acid sequences encoding transgenic CTLA4 or CTLA4-Ig can be used as donor cells to provide the nucleus for nuclear transfer into enucleated oocytes to produce cloned, transgenic animals. In one embodiment, the ungulate cell need not express the CTLA4 protein in order to be useful as a donor cell for nuclear transfer. In one embodiment, the porcine cell can be engineered to express CTLA4 from a nucleic acid construct or vector that contains a promoter. Alternatively, the porcine cells can be engineered to express CTLA4 under control of an endogenous promoter through homologous recombination. In one embodiment, the CTLA4 nucleic acid sequence can be inserted into the genome under the control of a tissue specific promoter, tissue specific enhancer or both. In another embodiment, the CTLA4 nucleic acid sequence can be inserted into the genome under the control of a ubiquitous promoter. In certain embodiments, targeting vectors are provided, which are designed to allow targeted homologous recombination in somatic cells. These targeting vectors can be transformed into mammalian cells to target the endogenous genes of interest via homologous recombination. In one embodiment, the targeting construct inserts both the CTLA4 nucleotide sequence and a selectable maker gene into the endogenous gene so as to be in reading frame with the upstream sequence and produce an active fusion protein. Cells can be transformed with the constructs using the methods of the invention and are selected by means of the selectable marker and then screened for the presence of recombinants.

The present invention provides a method for cloning an ungulate such as a pig containing CTLA4 peptides of the present invention via somatic cell nuclear transfer. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form nuclear transfer (NT) units; activating the resultant NT unit; and transferring said cultured NT unit to a host pig such that the NT unit develops into a fetus.

Nuclear transfer techniques or nuclear transplantation techniques are known in the art (see, for example, Campbell et al. (1995) Theriogenology, 43:181; Collas et al. (1994) Mol. Report Dev., 38:264-267; Keefer et al. (1994) Biol. Reprod., 50:935-939; Sims et al. (1993) Proc. Natl. Acad. Sci., USA, 90:6143-6147; WO 94/26884; WO 94/24274, and WO 90/03432, U.S. Pat. Nos. 4,944,384, 5,057,420, WO 97/07669, WO 97/07668, WO 98/30683, WO 00/22098, WO 004217, WO 00/51424, WO 03/055302, WO 03/005810, U.S. Pat. Nos. 6,147,276, 6,215,041, 6,235,969, 6,252,133, 6,258,998, 5,945,577, 6,525,243, 6,548,741, and Phelps et al. (Science 299:411-414 (2003)).

A donor cell nucleus, which has been modified to contain a CTLA4 gene of the present invention, is transferred to a recipient porcine oocyte. The use of this method is not restricted to a particular donor cell type. The donor cell can be as described in Wilmut et al. (1997) Nature 385:810; Campbell et al. (1996) Nature 380:64-66; or Cibelli et al. (1998) Science 280:1256-1258. All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell et al. (1995) Theriogenology 43:181, Collas et al. (1994) Mol. Reprod. Dev. 38:264-267, Keefer et al. (1994) Biol. Reprod. 50:935-939, Sims et al. (1993) Proc. Nat'l. Acad. Sci. USA 90:6143-6147, WO-A-9426884, WO-A-9424274, WO-A-9807841, WO-A-9003432, U.S. Pat. Nos. 4,994,384 and 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (see, for example, Campbell et al. (1996) Nature, 380:64-68) and Stice et al. (1996) Biol. Reprod., 20 54:100-

110). In a particular embodiment, fibroblast cells, such as porcine fibroblast cells can be genetically modified to contain transgenic CTLA4 as described in the present invention. In one embodiment, the CTLA4 constructs described herein can be transfected into the fibroblasts via electroporation or lipofection. Such fibroblast cells can be used as nuclear donors.

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration and in the case of porcine generally occurs at about 35-55 hours. This period of time is known as the "maturation period."

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, which ranges from about 10 to 40 hours, or particularly about 16-18 hours, the oocytes can be enucleated. Prior to enucleation the oocytes can be removed and placed in appropriate medium, such as HECM or TCM199 containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, for example not more than 24 hours later or 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, (1994) Mol. Reprod. Dev., 38:264-267. After fusion, the resultant fused NT units are then placed in a suitable medium until activation, for example, CR1aa medium. Typically activation can be effected shortly thereafter, for example less than 24 hours later, or about 4-9 hours later.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720 to Susko-Parrish et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's Whitten's media, PZM, NCSU23 and NCSU37. See Yoshioka K, Suzuki C, Tanaka A, Anas I M, Iwamura S. Biol Reprod.

(2002) January; 66(1):112-9 and Petters R M, Wells K D. J Reprod Fertil Suppl. 1993; 48:61-73;

Afterward, the cultured NT unit or units can be washed and then placed in a suitable media contained in well plates which can contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. NT units can be cultured until at least about 2 to 400 cells, about 4 to 128 cells, or at least about 50 cells.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. (1981) "Critical review of embryo transfer procedures with cattle" in Fertilization and Embryonic Development in Vitro, L. Mastroianni, Jr. and J. D. Biggers, ed., Plenum Press, New York, N.Y., page 323. Porcine embryo transfer can be conducted according to methods known in the art. For reference, see Youngs et al. "Factors Influencing the Success of Embryo Transfer in the Pig," *Theriogenology* (2002) 56: 1311-1320.

The following non-limiting examples serve to illustrate the present invention.

EXAMPLES

Example 1. Production of the pREV785 Construct

A construct was assembled containing the CTLA4-Ig transgene. The pREV785 construct contains the CTLA4-Ig transgene driven by the chicken beta actin promoter (ubiquitous expression) with additional enhancer and MAR sequences (FIG. 4). Complete sequence of the pREV785 plasmid comprising the pREV785 construct and associated vector backbone is shown in FIG. 5 (SEQ ID NO:4).

Example 2. Production of the pREV792 Construct

Figure 6:
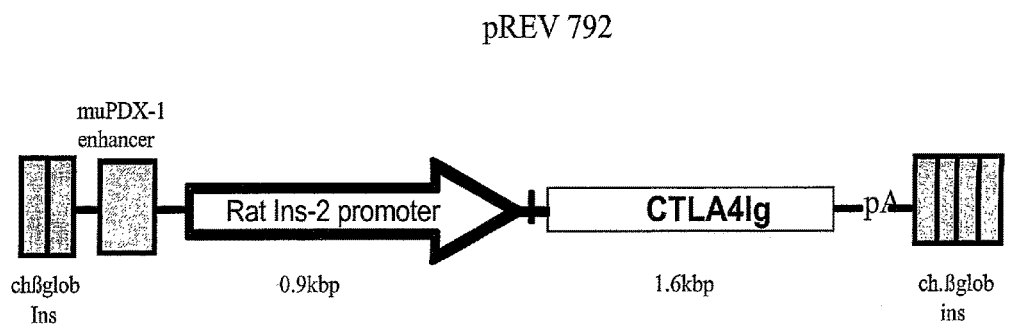
FIG. 6 depicts a schematic diagram of the pREV792 construct as described in Example 2.

A second construct was assembled containing the CTLA4-Ig transgene. The pREV792 construct contains the CTLA4-Ig transgene, driven by the rat insulin II promoter (tissue specific expression), with additional enhancer and insulator sequences (FIG. 6). Complete sequence of the pREV792 plasmid comprising the pREV792 construct and associated vector backbone is shown in FIG. 7 (SEQ ID NO:5).

Example 3. Transfection of Cells with the pREV785 Construct

A fetal fibroblast cell line (DPFA11) was isolated from a fetus at day 40 of gestation. Fetuses were mashed through a 60-mesh metal screen using curved surgical forceps slowly so as not to generate excessive heat. The cell suspension was then pelleted and resuspended in DMEM containing 20% fetal calf serum, 4 ng/ml basic fibroblast growth factor. Cells were cultured three days, and cryopreserved.

For transfection, three different linearized DNA vectors were simultaneously introduced into cells by electroporation. One was the pREV785 construct described in Example 1 (2 ug, linearized with PacI/Swa I), and one was a construct containing a human CD55 gene driven by the chicken beta actin promoter (pPL675) (1 ug). The third (pREV 784) was a construct comprising the hTFPI (human tissue factor pathway inhibitor) gene, the chicken beta actin promoter and the CMV enhancer.

Twenty-four hours following transfection, human CD55 transiently expressing cells were collected by flow cytometry, to enrich for presence of transfected DNA. These cells were cultured. After 4 days, the cultured cells were again assayed for human CD55 expression by flow cytometry and positive cells, which should contain stably integrated transgene DNA, were collected (1.8% expressed). Multiple non-linked transgenes can be effectively co-transfected by electroporation and can form concatemers and often co-integrate (Toneguzzo et al Nucleic Acids Res. 24; 16(12):5515-32, 1988). Therefore, some of these cells were expected to integrate both the CD55 construct and the pREV785 (CTLA4-Ig) construct, and some of the cells in this population were expected to be transgenic for the pREV785 CTLA4-Ig construct.

The presence of integrated pREV785 construct in the cell population was verified by PCR using primers (785.s and 785.a) targeting a 450 bp fragment extending from the globin splice site at the 3' end of the chicken beta actin promoter into the CTLA4-Ig sequence. The sequence of these primers was: 785.2s: gctggttgttgtgctgtctc (SEQ ID NO:7) and 785.2a: gaggtgccagtgcatgtaga (SEQ ID NO:8).

This population of cells was cryopreserved for future use as nuclear donors to produce CTLA4-Ig transgenic pigs by nuclear transfer.

Example 4. Transfection of Cells with the pREV792 Construct

A fetal fibroblast cell line (CD46SKO) was isolated from a fetus produced by mating two existing genetically modified pig lines. One pig line (CD46) was transgenic for the CD46 complement inhibitor gene. The other pig line (SKO) was heterozygous for disruption of the alpha 1,3 galactosyltransferase gene. On day 53 of gestation, fetuses were surgically isolated and mashed through a 60-mesh metal screen using curved surgical forceps slowly so as not to generate excessive heat. The cell suspension was then pelleted and resuspended in DMEM containing 20% fetal calf serum. Cells were cultured for one to two days, and cryopreserved. Cells were screened for the presence of the CD46 and SKO genetic modifications, and only those cell lines containing both modifications were used for further transfection as detailed below.

For transfection, three DNA vectors were simultaneously introduced into cells by electroporation. One was the pREV792 construct described in Example 2 (3 ug, linearized with AatII/Ase1), and one was a plasmid containing a human CD55 gene driven by the chicken beta actin promoter (1 ug) (pPL675). The third (pREV 790) was a construct comprising the hTFPI gene, the rat insulin 2 promoter and the PDX-1 enhancer. Forty-eight hours following transfection, human CD55 transiently expressing cells were collected by flow cytometry, to enrich for presence of transfected DNA. Resulting cells were cultured. After 5 days, the cultured cells were subcultured into 1152 wells at 4 cells per well (limiting dilution cloning). Eighty-eight colonies were harvested for PCR analysis after 8 days in culture.

The presence of integrated pREV792 construct in CD46SKO fetal fibroblast cells was determined by PCR using primers (792.s and 792.a) targeting a 473 bp fragment extending from the rat insulin II promoter into the 5' region of the CTLA4 coding sequence. The sequence of these primers was: 792.s: cgctgtgggctcttctcttacat (SEQ ID NO:9) and 792.a: gagcaagccatggctaagctta (SEQ ID NO:10).

Forty-nine of the 88 colonies harvested were PCR positive for the pREV792 construct. Cells from positively screened colonies were cryopreserved for future use as nuclear donors to produce CTLA4-Ig transgenic pigs by nuclear transfer.

Example 5. Production of Transgenic CTLAIg

Cell populations and cloned colonies that screen positive for the presence of a CTLA4-Ig construct (e.g. pREV785, pREV792) as described in Example 3 and 4, can be used as nuclear donors to produce CTLA4-Ig transgenic pigs by nuclear transfer.

The porcine nuclear transfer procedure can be performed as described by methods well known in the art (see, e.g. Dai et al., *Nature Biotechnology* 20:251-255, 2002; and Polejaeva et al., Nature 407:86-90, 2000). Enucleation of in vitro matured oocytes (Bomed, Madison, Wis.) can begin between 40 and 42 hours post-maturation. For enucleation, oocytes are incubated in M199 medium supplemented with 0.4% BSA, 7.5 µg/ml bisBezimide Hoechst 33342 (Sigma, cat# B-2661), 7.5 µg/ml Cytocalasin B (Sigma, cat# C-6762) at 38° C. for 20 minutes. Then a small amount of cytoplasm around the first polar body and the first polar body are aspirated using an 18-20 uM glass pipette (Humagen, Charlottesville, Va.). The aspirated karyoplast can be exposed to ultraviolet light to confirm the presence of a metaphase plate.

Donor cells (fetal or adult fibroblast cells) are cultured in Dulbecco's Modified Eagle Medium (DMEM, Gibco, cat#11995-065) supplemented with 10% fetal calf serum (Hyclone, Logan, Colo.) in a humidified incubator at 5% $O_2$, 5% $CO_2$ balanced with nitrogen. For culture, cells are seeded 3-7 days prior to the nuclear transfer procedure, at an appropriate dilution such that the cells will reach confluency 48 hours prior to nuclear transfer. On the day of nuclear transfer, donor cells are harvested about 30-45 minutes before reconstruction by using Trypsin-EDTA (Gibco, cat#25300-054), making a single cell suspension in suitable holding medium (e.g. Hepes buffered M199, Gibco cat #12350-039).

For nuclear transfer, a single fibroblast is placed under the zona pellucida in contact with each enucleated oocyte using a 22-28 uM glass pipette (Humagen). Fusion of the NT reconstructed embryo is induced by application of an AC pulse of 5V for 5 seconds followed by two DC pulses of 1.5 kV/cm for 60 pec, using an ECM2001 Electrocell Manipulator (BTX Inc., San Diego, Calif.) while embryos are in Fusion Medium (0.3M D-Mannitol, supplemented with 0.1 mM $MgSa_4$ and 0.1 mM $CaCl_2$ in $H_2O$). Fusion is checked visually approximately 30 minutes following the fusion procedure. Fused embryos are activated one-hour post fusion with two DC pulses of 1.25 kV/cm for 60 pec. During activation, NT embryos are held in Activation Medium (0.3M D-Mannitol, supplemented with 0.1 mM $MgSO_4$ and 0.05 mM $CaCl_2$ in $H_2O$). Fused and activated embryos are held in culture in Hepes buffered M199 medium for 1-4 hours post fusion in a dry bath incubator at 38.5°, and are then transferred to the oviduct of an estrus synchronized recipient gilt.

Crossbred gilts (Large white/Duroc/Landrace) (280-400 lbs) are synchronized as recipients by oral administration of 18-20 mg Matrix (Altrenogest, Hoechst, Warren, N.J.) mixed into their feed. Matrix is fed for 14 consecutive days. Human chorionic gonadotropin (hCG, 1,000 units; Intervet America, Millsboro, Del.) is administered intramuscularly 105 hours after the last Matrix treatment. Embryo transfers of NT reconstructed embryos is performed by mid-ventral laparotomy 22-26 hours after the hGC injection. Pregnancy can be maintained more effectively in recipients using a combination of Pregnant Mare Serum Gonadotropin, (PMSG, Calbiochem, San Diego, Calif.) and hCG injections. PMSG (1000 IU) is injected i.m. on day 10-11 post embryo transfer. hCG (500 IU) is injected i.m. 3-3.5 day later (day 13 post embryo transfer).

Genomic DNA from resulting piglets is screened by PCR to verify transgenic status using the primers 785.2s and 785.2a for pREV785, and primers 792.s and 792.a for pREV792. When a mixed population of transfected and screened cells is used as nuclear donors in the nuclear transfer procedure, not all of the resulting pigs will be transgenic. When limited dilution cloning is used, the probability of all piglets born being transgenic is greatly increased. Multiple rounds of nuclear transfer can be performed using the nuclear donor cells described herein resulting in a number of transgenic pigs that will contain a CTLA4 or CTLA4-Ig transgene and express CTLA4-Ig appropriately.

I claim:

1. A method of reducing cell mediated rejection of xenotransplanted cells in a recipient, comprising xenotransplanting genetically modified porcine cells into the recipient wherein:
   (i) the cell mediated rejection of the genetically modified porcine cells is reduced without suppression of the recipient's normal immune function;
   (ii) the genetically modified cells lack expression of the alpha-1,3-galactosyltransferase (alpha-1,3-GT) gene and express a transgene encoding a porcine CTLA4 peptide fused to a human immunoglobulin peptide (pCTLA4-Ig); and
   (iii) the genetically modified cells are directly obtained from a genetically modified porcine animal that lacks expression of the alpha-1,3-GT gene and expresses the pCTLA4-Ig peptide by insertion of the pCTLA4-Ig transgene into the genome of the animal.

2. The method of claim 1, wherein the CTLA4 peptide is truncated.

3. The method of claim 1, wherein the CTLA4 peptide is mutated.

4. The method of claim 1, wherein the CTLA4 peptide is mutated by substitution of (a) an alanine at position +29 with a tryptophan, and (b) a leucine at position +104 with a glutamic acid.

5. The method of claim 1, wherein the CTLA4 peptide is modified by the addition of an intracellular retention signal.

6. The method of claim 1, wherein the Ig is IgG.

7. The method of claim 1, wherein the IgG is IgG1 or IgG4.

8. The method of claim 1, wherein the cells are obtained from a tissue or organ of the porcine of claim 1.

9. The method of claim 1, further comprising administering soluble CTLA4 in addition to the genetically modified cells to the recipient.

10. The method of claim 9, wherein the soluble CTLA4 is porcine.

11. The method of claim 9, wherein the soluble CTLA4 is human.

* * * * *